US011969193B2

(12) United States Patent
Brumfield et al.

(10) Patent No.: US 11,969,193 B2
(45) Date of Patent: *Apr. 30, 2024

(54) INTRA-OSSEOUS PLATE SYSTEM AND METHOD

(71) Applicant: Treace Medical Concepts, Inc., Ponte Vedra, FL (US)

(72) Inventors: David L. Brumfield, Collierville, TN (US); Paul Dayton, Ankeny, IA (US); F. Barry Bays, Collierville, TN (US); Joe W. Ferguson, Ponte Vedra Beach, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/897,321

(22) Filed: Aug. 29, 2022

(65) Prior Publication Data

US 2022/0409250 A1    Dec. 29, 2022

Related U.S. Application Data

(63) Continuation of application No. 16/877,159, filed on May 18, 2020, now Pat. No. 11,426,219, which is a
(Continued)

(51) Int. Cl.
*A61B 17/80*   (2006.01)
*A61B 17/68*   (2006.01)
(Continued)

(52) U.S. Cl.
CPC ........ *A61B 17/8061* (2013.01); *A61B 17/686* (2013.01); *A61B 17/8014* (2013.01);
(Continued)

(58) Field of Classification Search
CPC ............ A61B 17/8061; A61B 17/8071; A61B 17/8095

See application file for complete search history.

(56) References Cited

U.S. PATENT DOCUMENTS 2,133,859 A   10/1938  Hawley
2,614,559 A   10/1952  Livingston
(Continued)

FOREIGN PATENT DOCUMENTS

AU    2009227957 B2    7/2014
CA       2491824 A1    9/2005
(Continued)

OTHER PUBLICATIONS

Defendant Fusion Orthopedics LLC's Invalidity Contentions, No. CV-22-00490-PHX-SRB, US District Court for the District of Arizona, Aug. 27, 2022, 41 pages.
(Continued)

*Primary Examiner* — Nicholas W Woodall
(74) *Attorney, Agent, or Firm* — Fredrikson & Byron, P.A.

(57) ABSTRACT

An intra-osseous support structure can be used to fixate opposed portions of bone. In some examples, the intra-osseous support structure is positioned in openings formed in adjacent portions of bones. Fasteners are inserted through the bone portions to secure the intra-osseous support structure in the bones. Depending on the application, one or more external bone plates may also be applied to the bone portions. The external bone plate may be in compression while the intra-osseous support structure is in tension under load in situ.

25 Claims, 13 Drawing Sheets

Related U.S. Application Data continuation of application No. 15/148,774, filed on May 6, 2016, now Pat. No. 10,653,467.

(60) Provisional application No. 62/157,561, filed on May 6, 2015.

(51) Int. Cl.
*A61B 17/88* (2006.01)
*A61B 17/064* (2006.01)
*A61B 17/86* (2006.01)

(52) U.S. Cl.
CPC ...... *A61B 17/8095* (2013.01); *A61B 17/8872* (2013.01); *A61B 17/0642* (2013.01); *A61B 17/86* (2013.01)

(56) References Cited

U.S. PATENT DOCUMENTS

| | | |
|---|---|---|
| 2,825,329 A | 3/1958 | Caesar |
| 3,709,218 A | 1/1973 | Halloran |
| 4,159,716 A | 7/1979 | Borchers |
| 4,187,840 A | 2/1980 | Watanabe |
| 4,338,927 A | 7/1982 | Volkov et al. |
| 4,570,624 A | 2/1986 | Wu |
| 4,627,425 A | 12/1986 | Reese |
| 4,628,919 A | 12/1986 | Clyburn |
| 4,754,746 A | 7/1988 | Cox |
| 4,757,810 A | 7/1988 | Reese |
| 4,790,302 A | 12/1988 | Colwill et al. |
| 4,895,141 A | 1/1990 | Koeneman et al. |
| 4,952,214 A | 8/1990 | Comparetto |
| 4,959,065 A | 9/1990 | Arnett et al. |
| 4,978,347 A | 12/1990 | Ilizarov |
| 4,988,349 A | 1/1991 | Pennig |
| 5,021,056 A | 6/1991 | Hofmann et al. |
| 5,112,334 A | 5/1992 | Alchermes et al. |
| 5,207,676 A | 5/1993 | Canadell et al. |
| 5,254,119 A | 10/1993 | Schreiber |
| 5,312,412 A | 5/1994 | Whipple |
| 5,358,504 A | 10/1994 | Paley et al. |
| 5,364,402 A | 11/1994 | Mumme et al. |
| 5,413,579 A | 5/1995 | Tom Du Toit |
| 5,417,694 A | 5/1995 | Marik et al. |
| 5,439,381 A | 8/1995 | Cohen |
| 5,449,360 A | 9/1995 | Schreiber |
| 5,529,075 A | 6/1996 | Clark |
| 5,586,564 A | 12/1996 | Barrett et al. |
| 5,620,442 A | 4/1997 | Bailey et al. |
| H1706 H | 1/1998 | Mason |
| 5,788,695 A | 8/1998 | Richardson |
| 5,803,924 A | 9/1998 | Oni et al. |
| 5,810,822 A | 9/1998 | Mortier |
| 5,893,553 A | 4/1999 | Pinkous |
| 5,935,128 A | 8/1999 | Carter et al. |
| 5,941,877 A | 8/1999 | Viegas et al. |
| 5,951,556 A | 9/1999 | Faccioli et al. |
| 6,030,391 A | 2/2000 | Brainard et al. |
| 6,162,223 A | 12/2000 | Orsak et al. |
| 6,171,309 B1 | 1/2001 | Huebner |
| 6,719,773 B1 | 4/2004 | Boucher et al. |
| 6,743,233 B1 | 6/2004 | Baldwin et al. |
| 7,001,388 B2 | 2/2006 | Orbay et al. |
| 7,033,361 B2 | 4/2006 | Collazo |
| 7,037,309 B2 | 5/2006 | Weil et al. |
| 7,037,342 B2 | 5/2006 | Nilsson et al. |
| 7,097,647 B2 | 8/2006 | Segler et al. |
| 7,153,310 B2 | 12/2006 | Ralph et al. |
| 7,182,766 B1 | 2/2007 | Mogul |
| 7,229,445 B2 | 6/2007 | Hayeck et al. |
| 7,241,298 B2 | 7/2007 | Nemec et al. |
| 7,377,924 B2 | 5/2008 | Raistrick et al. |
| 7,465,303 B2 | 12/2008 | Riccione et al. |
| 7,641,660 B2 | 1/2010 | Lakin et al. |
| D610,257 S | 2/2010 | Horton |
| 7,686,811 B2 | 3/2010 | Byrd et al. |
| D629,900 S | 12/2010 | Fisher |
| 7,972,338 B2 | 7/2011 | O'Brien |
| D646,389 S | 10/2011 | Claypool et al. |
| 8,057,478 B2 | 11/2011 | Kuczynski et al. |
| D651,315 S | 12/2011 | Bertoni et al. |
| D651,316 S | 12/2011 | May et al. |
| 8,080,010 B2 | 12/2011 | Schulz et al. |
| 8,123,753 B2 | 2/2012 | Poncet |
| 8,137,406 B2 | 3/2012 | Novak et al. |
| 8,147,530 B2 | 4/2012 | Strnad et al. |
| 8,167,918 B2 | 5/2012 | Strnad et al. |
| 8,172,848 B2 | 5/2012 | Tomko et al. |
| 8,177,820 B2 | 5/2012 | Anapliotis et al. |
| 8,192,441 B2 | 6/2012 | Collazo |
| 8,197,487 B2 | 6/2012 | Poncet et al. |
| 8,231,623 B1 | 7/2012 | Jordan |
| 8,231,663 B2 | 7/2012 | Kay et al. |
| 8,246,561 B1 | 8/2012 | Agee et al. |
| D666,721 S | 9/2012 | Wright et al. |
| 8,262,664 B2 | 9/2012 | Justin et al. |
| 8,282,644 B2 | 10/2012 | Edwards |
| 8,282,645 B2 | 10/2012 | Lawrence et al. |
| 8,292,966 B2 | 10/2012 | Morton |
| 8,313,492 B2 | 11/2012 | Wong et al. |
| 8,323,289 B2 | 12/2012 | Re |
| 8,337,503 B2 | 12/2012 | Lian |
| 8,343,159 B2 | 1/2013 | Bennett |
| 8,377,105 B2 | 2/2013 | Bscher |
| 8,382,807 B2 | 2/2013 | Austin et al. |
| 8,403,966 B2 | 3/2013 | Ralph et al. |
| D679,395 S | 4/2013 | Wright et al. |
| 8,435,246 B2 | 5/2013 | Fisher et al. |
| 8,475,462 B2 | 7/2013 | Thomas et al. |
| 8,496,690 B2 | 7/2013 | Sixto et al. |
| 8,523,870 B2 | 9/2013 | Green, II et al. |
| 8,556,946 B2 * | 10/2013 | Prandi ............... A61B 17/8004 606/286 |
| D694,884 S | 12/2013 | Mooradian et al. |
| D695,402 S | 12/2013 | Dacosta et al. |
| 8,652,142 B2 | 2/2014 | Geissler |
| D701,303 S | 3/2014 | Cook |
| 8,672,945 B2 | 3/2014 | Lavallee et al. |
| 8,696,716 B2 | 4/2014 | Kartalian et al. |
| D705,929 S | 5/2014 | Frey |
| 8,715,363 B2 | 5/2014 | Ratron et al. |
| 8,728,084 B2 | 5/2014 | Berelsman et al. |
| 8,758,354 B2 | 6/2014 | Habegger et al. |
| 8,764,763 B2 | 7/2014 | Wong et al. |
| 8,771,279 B2 | 7/2014 | Philippon et al. |
| 8,784,427 B2 | 7/2014 | Fallin et al. |
| 8,784,457 B2 * | 7/2014 | Graham ............... A61B 17/809 606/286 |
| 8,795,286 B2 | 8/2014 | Sand et al. |
| 8,801,727 B2 | 8/2014 | Chan et al. |
| 8,808,303 B2 | 8/2014 | Stemniski et al. |
| 8,828,012 B2 | 9/2014 | May et al. |
| 8,828,063 B2 * | 9/2014 | Blitz ............... A61B 17/8085 606/283 |
| 8,858,602 B2 | 10/2014 | Weiner et al. |
| 8,882,778 B2 | 11/2014 | Ranft |
| 8,888,824 B2 | 11/2014 | Austin et al. |
| 8,911,482 B2 | 12/2014 | Lee et al. |
| 8,940,026 B2 | 1/2015 | Hilse et al. |
| 8,998,903 B2 | 4/2015 | Price et al. |
| 8,998,904 B2 | 4/2015 | Zeetser et al. |
| 9,023,052 B2 | 5/2015 | Lietz et al. |
| 9,044,250 B2 | 6/2015 | Olsen et al. |
| 9,060,822 B2 * | 6/2015 | Lewis ............... A61B 17/8605 |
| 9,089,376 B2 | 7/2015 | Medoff et al. |
| 9,101,421 B2 | 8/2015 | Blacklidge |
| 9,107,715 B2 | 8/2015 | Blitz et al. |
| 9,138,244 B2 | 9/2015 | Mebarak et al. |
| 9,271,769 B2 | 3/2016 | Batsch et al. |
| D765,844 S | 9/2016 | DaCosta |
| D766,434 S | 9/2016 | DaCosta |
| D766,437 S | 9/2016 | DaCosta |
| D766,438 S | 9/2016 | DaCosta |
| D766,439 S | 9/2016 | DaCosta |

(56) References Cited

U.S. PATENT DOCUMENTS

| | | |
|---|---|---|
| 9,452,057 B2 | 9/2016 | Dacosta et al. |
| 9,642,656 B2 | 5/2017 | Kotuljac et al. |
| 9,668,793 B2 | 6/2017 | Gaudin |
| 9,750,538 B2 | 9/2017 | Soffiatti et al. |
| 9,867,642 B2 | 1/2018 | Simon |
| 9,980,760 B2 | 5/2018 | Dacosta et al. |
| 10,226,287 B2 | 3/2019 | Langford et al. |
| 10,238,437 B2 | 3/2019 | Simon |
| 10,376,268 B2 | 8/2019 | Fallin et al. |
| 11,304,705 B2 | 4/2022 | Fallin et al. |
| 2002/0099381 A1 | 7/2002 | Maroney |
| 2002/0107519 A1 | 8/2002 | Dixon et al. |
| 2002/0198531 A1 | 12/2002 | Millard et al. |
| 2003/0135212 A1 | 7/2003 | Chow |
| 2004/0010259 A1 | 1/2004 | Keller et al. |
| 2004/0039394 A1 | 2/2004 | Conti et al. |
| 2004/0097946 A1 | 5/2004 | Dietzel et al. |
| 2005/0004676 A1 | 1/2005 | Schon et al. |
| 2005/0075641 A1 | 4/2005 | Singhatat et al. |
| 2005/0101961 A1 | 5/2005 | Huebner et al. |
| 2005/0149042 A1 | 7/2005 | Metzger |
| 2005/0228389 A1 | 10/2005 | Stiernborg |
| 2005/0267482 A1 | 12/2005 | Hyde, Jr. |
| 2005/0273112 A1 | 12/2005 | McNamara |
| 2006/0206044 A1 | 9/2006 | Simon |
| 2006/0217733 A1 | 9/2006 | Plassky et al. |
| 2006/0229621 A1 | 10/2006 | Cadmus |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2007/0123857 A1 | 5/2007 | Deffenbaugh et al. |
| 2007/0233138 A1 | 10/2007 | Figueroa et al. |
| 2007/0265634 A1 | 11/2007 | Weinstein |
| 2007/0276383 A1 | 11/2007 | Rayhack |
| 2008/0091197 A1 | 4/2008 | Coughlin |
| 2008/0140081 A1 | 6/2008 | Heavener et al. |
| 2008/0172054 A1 | 7/2008 | Claypool et al. |
| 2008/0208252 A1 | 8/2008 | Holmes |
| 2008/0262500 A1 | 10/2008 | Collazo |
| 2008/0269908 A1 | 10/2008 | Warburton |
| 2009/0036893 A1 | 2/2009 | Kartalian et al. |
| 2009/0093849 A1 | 4/2009 | Grabowski |
| 2009/0105767 A1 | 4/2009 | Reiley |
| 2009/0118733 A1 | 5/2009 | Orsak et al. |
| 2009/0198244 A1 | 8/2009 | Leibel |
| 2009/0198279 A1 | 8/2009 | Zhang et al. |
| 2009/0222047 A1 | 9/2009 | Graham |
| 2009/0254092 A1 | 10/2009 | Albiol Llorach |
| 2009/0254126 A1 | 10/2009 | Orbay et al. |
| 2009/0287309 A1 | 11/2009 | Walch et al. |
| 2009/0312802 A1 | 12/2009 | Dasilva |
| 2010/0069910 A1 | 3/2010 | Hasselman |
| 2010/0121334 A1 | 5/2010 | Couture et al. |
| 2010/0130981 A1 | 5/2010 | Richards |
| 2010/0152782 A1 | 6/2010 | Stone et al. |
| 2010/0168799 A1 | 7/2010 | Schumer |
| 2010/0185245 A1 | 7/2010 | Paul et al. |
| 2010/0249779 A1 | 9/2010 | Hotchkiss et al. |
| 2010/0256687 A1* | 10/2010 | Neufeld ............ A61B 17/8061 606/280 |
| 2010/0324556 A1 | 12/2010 | Tyber et al. |
| 2011/0087295 A1 | 4/2011 | Kubiak et al. |
| 2011/0093084 A1 | 4/2011 | Morton |
| 2011/0245835 A1 | 10/2011 | Dodds et al. |
| 2011/0288550 A1 | 11/2011 | Orbay et al. |
| 2011/0301648 A1 | 12/2011 | Lofthouse et al. |
| 2012/0016426 A1 | 1/2012 | Robinson |
| 2012/0065689 A1 | 3/2012 | Prasad et al. |
| 2012/0078258 A1 | 3/2012 | Lo et al. |
| 2012/0123420 A1 | 5/2012 | Honiball |
| 2012/0123484 A1 | 5/2012 | Lietz et al. |
| 2012/0130376 A1 | 5/2012 | Loring et al. |
| 2012/0130383 A1 | 5/2012 | Budoff |
| 2012/0184961 A1 | 7/2012 | Johannaber |
| 2012/0239045 A1 | 9/2012 | Li |
| 2012/0253350 A1 | 10/2012 | Anthony et al. |
| 2012/0265301 A1 | 10/2012 | Demers et al. |
| 2012/0277745 A1 | 11/2012 | Lizee et al. |
| 2012/0303033 A1 | 11/2012 | Weiner et al. |
| 2012/0330135 A1 | 12/2012 | Millahn et al. |
| 2013/0012949 A1 | 1/2013 | Fallin et al. |
| 2013/0035694 A1 | 2/2013 | Grimm et al. |
| 2013/0085499 A1 | 4/2013 | Lian |
| 2013/0096563 A1 | 4/2013 | Meade et al. |
| 2013/0150900 A1 | 6/2013 | Haddad et al. |
| 2013/0150903 A1 | 6/2013 | Vincent |
| 2013/0158556 A1 | 6/2013 | Jones et al. |
| 2013/0165936 A1 | 6/2013 | Myers |
| 2013/0165938 A1 | 6/2013 | Chow et al. |
| 2013/0172942 A1 | 7/2013 | Lewis et al. |
| 2013/0184714 A1 | 7/2013 | Kaneyama et al. |
| 2013/0190765 A1 | 7/2013 | Harris et al. |
| 2013/0190766 A1 | 7/2013 | Harris et al. |
| 2013/0204259 A1 | 8/2013 | Zajac |
| 2013/0231668 A1 | 9/2013 | Olsen et al. |
| 2013/0237987 A1 | 9/2013 | Graham |
| 2013/0237989 A1 | 9/2013 | Bonutti |
| 2013/0267956 A1 | 10/2013 | Terrill et al. |
| 2013/0310836 A1 | 11/2013 | Raub et al. |
| 2013/0325019 A1 | 12/2013 | Thomas et al. |
| 2013/0325076 A1 | 12/2013 | Palmer et al. |
| 2013/0331845 A1 | 12/2013 | Horan et al. |
| 2013/0338785 A1 | 12/2013 | Wong |
| 2014/0005672 A1 | 1/2014 | Edwards et al. |
| 2014/0025127 A1 | 1/2014 | Richter |
| 2014/0039501 A1 | 2/2014 | Schickendantz et al. |
| 2014/0039561 A1 | 2/2014 | Weiner et al. |
| 2014/0046387 A1 | 2/2014 | Waizenegger |
| 2014/0074099 A1 | 3/2014 | Vigneron et al. |
| 2014/0074101 A1 | 3/2014 | Collazo |
| 2014/0094861 A1 | 4/2014 | Fallin |
| 2014/0094924 A1 | 4/2014 | Hacking et al. |
| 2014/0163563 A1 | 6/2014 | Reynolds et al. |
| 2014/0171953 A1 | 6/2014 | Gonzalvez et al. |
| 2014/0180342 A1 | 6/2014 | Lowery et al. |
| 2014/0194884 A1 | 7/2014 | Martin et al. |
| 2014/0207144 A1 | 7/2014 | Lee et al. |
| 2014/0214037 A1 | 7/2014 | Mayer et al. |
| 2014/0249537 A1 | 9/2014 | Wong et al. |
| 2014/0257509 A1 | 9/2014 | Dacosta et al. |
| 2014/0276815 A1 | 9/2014 | Riccione |
| 2014/0276853 A1 | 9/2014 | Long et al. |
| 2014/0277176 A1 | 9/2014 | Buchanan et al. |
| 2014/0277214 A1 | 9/2014 | Helenbolt et al. |
| 2014/0296995 A1 | 10/2014 | Reiley et al. |
| 2014/0303621 A1 | 10/2014 | Gerold et al. |
| 2014/0336658 A1 | 11/2014 | Luna et al. |
| 2014/0350561 A1 | 11/2014 | Dacosta et al. |
| 2015/0032168 A1 | 1/2015 | Orsak et al. |
| 2015/0045801 A1 | 2/2015 | Axelson, Jr. et al. |
| 2015/0045839 A1 | 2/2015 | Dacosta et al. |
| 2015/0051650 A1 | 2/2015 | Verstreken et al. |
| 2015/0066094 A1 | 3/2015 | Prandi et al. |
| 2015/0112446 A1 | 4/2015 | Melamed et al. |
| 2015/0119944 A1 | 4/2015 | Geldwert |
| 2015/0142064 A1 | 5/2015 | Perez et al. |
| 2015/0150608 A1 | 6/2015 | Sammarco |
| 2015/0182273 A1 | 7/2015 | Stemniski et al. |
| 2015/0223851 A1 | 8/2015 | Hill et al. |
| 2015/0245858 A1 | 9/2015 | Weiner et al. |
| 2016/0015426 A1 | 1/2016 | Dayton et al. |
| 2016/0022315 A1 | 1/2016 | Soffiatti et al. |
| 2016/0135858 A1 | 5/2016 | Dacosta et al. |
| 2016/0151165 A1 | 6/2016 | Fallin et al. |
| 2016/0175089 A1 | 6/2016 | Fallin et al. |
| 2016/0192950 A1 | 7/2016 | Dayton et al. |
| 2016/0199076 A1 | 7/2016 | Fallin et al. |
| 2016/0213384 A1 | 7/2016 | Fallin et al. |
| 2016/0235414 A1 | 8/2016 | Hatch et al. |
| 2016/0242791 A1 | 8/2016 | Fallin et al. |
| 2016/0256204 A1 | 9/2016 | Patel et al. |
| 2016/0354127 A1 | 12/2016 | Lundquist et al. |
| 2017/0000533 A1 | 1/2017 | Fallin et al. |
| 2017/0042599 A1 | 2/2017 | Bays et al. |

(56) References Cited

U.S. PATENT DOCUMENTS

| | | |
|---|---|---|
| 2017/0079669 A1 | 3/2017 | Bays et al. |
| 2018/0132868 A1 | 5/2018 | Dacosta et al. |
| 2018/0344334 A1 | 12/2018 | Kim et al. |
| 2018/0344371 A1 | 12/2018 | Monk et al. |
| 2019/0357950 A1 | 11/2019 | Bernstein et al. |

FOREIGN PATENT DOCUMENTS

| | | |
|---|---|---|
| CA | 2854997 A1 | 5/2013 |
| CH | 695846 A5 | 9/2006 |
| CN | 2930668 Y | 8/2007 |
| CN | 201558162 U | 8/2010 |
| CN | 201572172 U | 9/2010 |
| CN | 201586060 U | 9/2010 |
| CN | 201912210 U | 8/2011 |
| CN | 202801773 U | 3/2013 |
| CN | 103462675 A | 12/2013 |
| CN | 103505276 A | 1/2014 |
| CN | 203458450 U | 3/2014 |
| CN | 102860860 B | 5/2014 |
| CN | 203576647 U | 5/2014 |
| CN | 104490460 A | 4/2015 |
| CN | 104510523 A | 4/2015 |
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |
| CN | 204428145 U | 7/2015 |
| CN | 204446081 U | 7/2015 |
| EP | 685206 B1 | 9/2000 |
| EP | 1897509 B1 | 7/2009 |
| EP | 2124772 A1 | 12/2009 |
| EP | 2124832 B1 | 8/2012 |
| EP | 2632349 A1 | 9/2013 |
| EP | 2665428 A1 | 11/2013 |
| EP | 2742878 A1 | 6/2014 |
| EP | 2750617 A1 | 7/2014 |
| EP | 2849684 A1 | 3/2015 |
| EP | 3023068 A2 | 5/2016 |
| FR | 2362616 A1 | 3/1978 |
| FR | 2764183 B1 | 11/1999 |
| FR | 3030221 A1 | 6/2016 |
| GB | 2154143 A | 9/1985 |
| GB | 2154144 A | 9/1985 |
| IN | 200903719 P1 | 6/2009 |
| IN | 200904479 P2 | 5/2010 |
| IN | 140/DELNP/2012 P1 | 2/2013 |
| IN | 2004/KOLNP/2013 P2 | 11/2013 |
| JP | 4134243 B2 | 8/2008 |
| JP | 4162380 B2 | 10/2008 |
| JP | 2011092405 A | 5/2011 |
| JP | 2011523889 A | 8/2011 |
| JP | 4796943 B2 | 10/2011 |
| JP | 5466647 B2 | 4/2014 |
| JP | 2014511207 A | 5/2014 |
| JP | 2014521384 A | 8/2014 |
| JP | 5628875 B2 | 11/2014 |
| KR | 100904142 B1 | 6/2009 |
| MD | 756 Z | 11/2014 |
| RU | 2098036 C1 | 12/1997 |
| RU | 2195892 C2 | 1/2003 |
| RU | 2320287 C1 | 3/2008 |
| RU | 2321366 C2 | 4/2008 |
| RU | 2321369 C1 | 4/2008 |
| RU | 2346663 C2 | 2/2009 |
| RU | 2412662 C1 | 2/2011 |
| SU | 1333328 A2 | 8/1987 |
| WO | 0166022 A1 | 9/2001 |
| WO | 2008051064 A1 | 5/2008 |
| WO | 2009029798 A1 | 3/2009 |
| WO | 2009032101 A2 | 3/2009 |
| WO | 2011037885 A1 | 3/2011 |
| WO | 2012029008 A1 | 3/2012 |
| WO | 2013090392 A1 | 6/2013 |
| WO | 2013134387 A1 | 9/2013 |
| WO | 2013169475 A1 | 11/2013 |
| WO | 2014020561 A1 | 2/2014 |
| WO | 2014022055 A1 | 2/2014 |
| WO | 2014035991 A1 | 3/2014 |
| WO | 2014085882 A1 | 6/2014 |
| WO | 2014147099 A1 | 9/2014 |
| WO | 2014152219 A2 | 9/2014 |
| WO | 2014152535 A1 | 9/2014 |
| WO | 2014177783 A1 | 11/2014 |
| WO | 2014200017 A1 | 12/2014 |
| WO | 2015105880 A1 | 7/2015 |
| WO | 2015127515 A2 | 9/2015 |

OTHER PUBLICATIONS

Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
Claim Chart for U.S. Pat. No. 10,376,268 to Fallin et al., entitled "Indexed Tri-Planar Osteotomy Guide and Method," Issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.
Obviousness Chart, Exhibit C of Defendant Fusion Orthopedics LLC's Invalidity Contentions, No. CV-22-00490-PHX-SRB, US District Court for the District of Arizona, Aug. 27, 2022, 153 pages.
"Foot and Ankle Instrument Set," Smith & Nephew, 2013, 2 pages.
"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.
"Reconstructive Surgery of the Foot & Ankle," The Podiatry Institute, Update 2015, Conference Program, May 2015, 28 pages.
"Speed Continuous Active Compression Implant," BioMedical Enterprises, Inc., A120-029 Rev. 3, 2013, 4 pages.
"Visionaire: Patient Matched Cutting Blocks Surgical Procedure," Smith & Nephew, Inc., 2009, 2 pages.
Arthrex, "Comprehensive Foot System," Retrieved online from <https://www.arthrex.com/resources/animation/8U3iaPvY6kO8bwFAwZF50Q/comprehensive-foot-system?referringTeam=foot_and_ankle>, dated Aug. 27, 2013, 3 pages.

(56) References Cited

OTHER PUBLICATIONS

Baravarian, "Why the Lapidus Procedure is Ideal for Bunions," Podiatry Today, Retrieved online from <https://www.hmpgloballearhmpgloballe.com/site/podipodi/article/5542>, dated May 2006, 8 pages.
Bauer et al., "Offset-V Osteotomy of the First Metatarsal Shaft in Hallux Abducto Valgus, " McGlamry's Comprehensive Textbook of Foot and Ankle Surgery, Fourth Edition, vol. 1, Chapter 29, 2013, 26 pages.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Coughlin, "Fixation of the Lapidus Arthrodesis with a Plantar Interfragmentary Screw and Medial Low Profile Locking Plate, "Orthopaedics and Traumatology, vol. 7, 1999, pp. 133-143.
Dayton et al., "Observed Changes in Radiographic Measurements of the First Ray after Frontal Plane Rotation of the First Metatarsal in a Cadaveric Foot Model," The Journal of Foot & Ankle Surgery, vol. 53, 2014, pp. 274-278.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.
DiDomenico et al., "Lapidus Bunionectomy: First MetatarsalCuneiform Arthrodesis," McGlamry's Comprehensive Textbook of Foot and Ankle Surgery, Fourth Edition, vol. 1, Chapter 31, 2013, 24 pages.
Fallin et al., US Provisional Application Entitled Indexed Tri-Planar Osteotomy Guide and Method, U.S. Appl. No. 62/118,378, filed Feb. 19, 2015, 62 pages.
Fishco, "A Straightforward Guide To The Lapidus Bunionectomy, "Podiatry Today, Retrieved online from <https://www.hmpgloballearningnetwork.com/site/podiatry/blogged/straightforwardguide-lapidus-bunionectomy>, dated Sep. 6, 2013, 5 pages.
Fishco, "Making the Lapidus Easy," The Podiatry Institute, Update 2014, Chapter 14, 2014, pp. 91-93.
Fleming et al., "Results of Modified Lapidus Arthrodesis Procedure Using Medial Eminence as an Interpositional Autograft," The Journal of Foot & Ankle Surgery, vol. 50, 2011, pp. 272-275.
Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.
Gerard et al., "The Modified Lapidus Procedure," Orthopedics, vol. 31, No. 3, Mar. 2008, 7 pages.
Giannoudis et al., "Hallux Valgus Correction," Practical Procedures in Elective Orthopaedic Surgery, Pelvis and Lower Extremity, Chapter 38, 2012, 22 pages.
Greiner, "The Jargon of Pedal Movements," Foot & Ankle International, vol. 28, No. 1, Jan. 2007, pp. 109-125.
Groves, "Functional Position Joint Sectioning: Pre-Load Method for Lapidus Arthrodesis," The Podiatry Institute, Update 2015, Chapter 6, 2015, pp. 23-29.
Hardy et al., "Observations on Hallux Valgus," The Journal of Bone and Joint Surgery, vol. 33B, No. 3, Aug. 1951, pp. 376-391.
Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.
Integra, "Integra Large Qwix Positioning and Fixation Screw, Surgical Technique," 2012, 16 pages.
Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.
Lee et al., "Technique Tip: Lateral Soft-Tissue Release for Correction of Hallux Valgus Through a Medial Incision Using A Dorsal Flap Over the First Metatarsal," Foot & Ankle International, vol. 28, No. 8, Aug. 2007, pp. 949-951.
Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.
Myerson, "Cuneiform-Metatarsal Arthrodesis," The Foot and Ankle, Chapter 9, 1997, pp. 107-117.
Sammarco, "Surgical Strategies: Mau Osteotomy for Correction of Moderate and Severe Hallux Valgus Deformity," Foot & Ankle International, vol. 28, No. 7, Jul. 2007, pp. 857-864.
Schon et al., "Cuneiform-Metatarsal Arthrodesis for Hallux Valgus, "The Foot and Ankle, Second Edition, Chapter 8, 2002, pp. 99-117.
Sokoloff, "Lapidus Procedure," Textbook of Bunion Surgery, Chapter 15, 1981, pp. 277-287.
Stamatis et al., "Mini Locking Plate as "Medial Buttress" for Oblique Osteotomy for Hallux Valgus," Foot & Ankle International, vol. 31, No. 10, Oct. 2010, pp. 920-922.
Stewart, "Use for BME Speed Nitinol Staple Fixation for the Lapidus Procedure," date unknown, 1 page.
Wukich et al., "Hypermobility of the First Tarsometatarsal Joint," Foot and Ankle Clinics, vol. 10, No. 1, Mar. 2005, pp. 157-166.
Dayton et al., "Biwinged Excision for Round Pedal Lesions," The Journal of Foot and Ankle Surgery, vol. 35, No. 3, 1996, pp. 244-249.
Dayton et al., "Medial Incision Approach to the First Metatarsophalangeal Joint," The Journal of Foot and Ankle Surgery, vol. 40, No. 6, Nov./Dec. 2001, pp. 414-417.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp. 167-169.
Dayton et al., "Early Weightbearing After First Metatarsophalangeal Joint Arthrodesis: A Retrospective Observational Case Analysis, " The Journal of Foot and Ankle Surgery, vol. 43, No. 3, May/Jun. 2004, pp. 156-159.
Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.
Dayton et al., "The Extended Knee Hemilithotomy Position for Gastrocnemius Recession," The Journal of Foot and Ankle Surgery, vol. 49, 2010, pp. 214-216.
Wienke et al., "Bone Stimulation For Nonunions: What the Evidence Reveals," Podiatry Today, vol. 24, No. 9, Sep. 2011, pp. 52-57.
Dayton et al., "Hallux Varus as Complication of Foot Compartment Syndrome," The Journal of Foot and Ankle Surgery, vol. 50, 2011, pp. 504-506.
Dayton et al., "Measurement of Mid-Calcaneal Length on Plain Radiographs: Reliability of a New Method," Foot and Ankle Specialist, vol. 4, No. 5, Oct. 2011, pp. 280-283.
Dayton et al., "A User-Friendly Method of Pin Site Management for External Fixators," Foot and Ankle Specialist, Sep. 16, 2011, 4 pages.
Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.
Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.
Dayton et al., "Technique for Minimally Invasive Reduction of Calcaneal Fractures Using Small Bilateral External Fixation," The Journal of Foot and Ankle Surgery, Article in Press, 2014, 7 pages.
Dayton et al., "Clarification of the Anatomic Definition of the Bunion Deformity," The Journal of Foot and Ankle Surgery, vol. 53, 2014, pp. 160-163.
Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.

(56) References Cited

OTHER PUBLICATIONS

Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.
Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.
Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.
Dayton et al., "Principles of Management of Growth Plate Fractures in the Foot and Ankle," Clinics in Podiatric Medicine and Surgery, Pediatric Foot Deformities, Oct. 2013, 17 pages.
Dayton et al., "Observed Changes in Radiographic Measurements of the First Ray after Frontal and Transverse Plane Rotation of the Hallux: Does the Hallux Drive the Metatarsal in a Bunion Deformity? ," The Journal of Foot and Ankle Surgery, Article in Press, 2014, 4 pages.
Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.
Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.
Catanese et al., "Measuring Sesamoid Position in Hallux Valgus: When Is the Sesamoid Axial View Necessary," Foot and Ankle Specialist, 2014, 3 pages.
Dayton et al., "Comparison of Complications for Internal and External Fixation for Charcot Reconstruction: A Systematic Review," The Journal of Foot and Ankle Surgery, Article in Press, 2015, 4 pages.
Dayton et al., "A new triplanar paradigm for bunion management," Lower Extremity Review, Apr. 2015, 9 pages.
Dayton et al., "American College of Foot and Ankle Surgeons' Clinical Consensus Statement: Perioperative Prophylactic Antibiotic Use in Clean Elective Foot Surgery," The Journal of Foot and Ankle Surgery, Article in Press, 2015, 7 pages.
Dayton et al., "Complications of Metatarsal Suture Techniques for Bunion Correction: A Systematic Review of the Literature," The Journal of Foot and Ankle Surgery, Article in Press, 2015, 3 pages.
DeCarbo et al., "The Weil Osteotomy: A Refresher," Techniques in Foot and Ankle Surgery, vol. 13, No. 4, Dec. 2014, pp. 191-198.
DeCarbo et al., "Resurfacing Interpositional Arthroplasty for Degenerative Joint Diseas of the First Metatarsalphalangeal Joint," Podiatry Management, Jan. 2013, pp. 137-142.
DeCarbo et al., "Locking Plates: Do They Prevent Complications?," Podiatry Today, Apr. 2014, 7 pages.
Easley et al., "Current Concepts Review: Hallux Valgus Part II: Operative Treatment," Foot and Ankle International, vol. 28, No. 6, Jun. 2007, pp. 748-758.
Kim et lal., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.
Easley et al., "Current Concepts Review: Hallux Valgus Part I: Pathomechanics, Clinical Assessment, and Nonoperative Management," Foot and Ankle International, vol. 28, No. 5, May 2007, pp. 654-659.
Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.
Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.

Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.
Easley et al., "What is the Best Treatment for Hallux Valgus?," Evidence-Based Orthopaedics - The Best Answers to Clinical Questions, Chapter 73, 2009, pp. 479-491.
Shurnas et al., "Proximal Metatarsal Opening Wedge Osteotomy," Operative Techniques in Foot and Ankle Surgery, Section I, Chapter 13, 2011, pp. 73-78.
Coetzee et al., "Revision Hallux Valgus Correction," Operative Techniques in Foot and Ankle Surgery, Section I, Chapter 15, 2011, pp. 84-96.
Le et al., "Tarsometatarsal Arthrodesis," Operative Techniques in Foot and Ankle Surgery, Section II, Chapter 40, 2011, pp. 281-285.
Collan et al., "The biomechanics of the first metatarsal bone in hallux valgus: A preliminary study utilizing a weight bearing extremity CT," Foot and Ankle Surgery, vol. 19, 2013, pp. 155-161.
Eustace et al., "Hallux valgus, first metatarsal pronation and collapse of the medial longitudinal arch—a radiological correlation," Skeletal Radiology, vol. 23, 1994, pp. 191-194.
Mizuno et al., "Detorsion Osteotomy of the First Metatarsal Bone in Hallux Valgus," Japanese Orthopaedic Association, Tokyo, 1956; 30:813-819.
Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.
Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.
D'Amico et al., "Motion of the First Ray: Clarification Through Investigation," Journal of the American Podiatry Association, vol. 69, No. 1, Jan. 1979, pp. 17-23.
Groves, "Operative Report," St. Tammany Parish Hospital, Date of Procedure, Mar. 26, 2014, 2 pages.
Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.
Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.
Anderson et al., "Uncemented STAR Total Ankle Prostheses," The Journal of Bone and Joint Surgery, vol. 86(1, Suppl 2), Sep. 2004, pp. 103-111, (Abstract Only).
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Observed Changes in Radiographic Measurements of the First Ray after Frontal and Transverse Plane Rotation of the Hallux: Does the Hallux Drive the Metatarsal in a Bunion Deformity? ," The Journal of Foot and Ankle Surgery, vol. 53, 2014, pp. 584-587.
Dayton et al., "Relationship Of Frontal Plane Rotation Of First Metatarsal To Proximal Articular Set Angle And Hallux Alignment In Patients Undergoing Tarsometatarsal Arthrodesis For Hallux Abducto Valgus: A Case Series And Critical Review Of The Literature," The Journal of Foot and Ankle Surgery, vol. 52, No. 3, May/Jun. 2013, pp. 348-354.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
Didomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.

(56) References Cited

OTHER PUBLICATIONS

Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).
EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.
Garthwait, "Accu-Cut System Facilitates Enhanced Precision," Podiatry Today, vol. 18, No. 6, Jun. 2005, 6 pages.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.
Grondal et al., "A Guide Plate for Accurate Positioning of First Metatarsophalangeal Joint during Fusion," Operative Orthopädie Und Traumatologie, vol. 16, No. 2, 2004, pp. 167-178 (Abstract Only).
"Hat-Trick Lesser Toe Repair System," Smith & Nephew, Brochure, Aug. 2014, 12 pages.
"Hoffmann II Compact External Fixation System," Stryker, Brochure, Literature No. 5075-1-500, 2006, 12 pages.
"Hoffmann II Micro Lengthener," Stryker, Operative Technique, Literature No. 5075-2-002, 2008, 12 pages.
"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.
Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.
"Lag Screw Target Bow," Stryker Leibinger GmbH & Co. KG, Germany 2004, 8 pages.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Michelangelo Bunion System, Surgical Technique, Instratek Incorporated, publication date unknown, 4 pages.
Mini Joint Distractor, Arthrex, retrieved Dec. 19, 2014, from the Internet: <http://www.arthrex.com/foot-ankle/mini-joint-distractor/products>, 2 pages.
MiniRail System, Small Bone Innovations, Surgical Technique, 2010, 24 pages.
Modular Rail System: External Fixator, Smith & Nephew, Surgical Technique, 2013, 44 pages.
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect Of Ankle Flexion Angle On Axial Alignment Of Total Ankle Replacement," Foot and Ankle International, vol. 31, No. 12, Dec. 2010, pp. 1093-1098, (Abstract Only).
Mortier et al., "Axial Rotation of the First Metatarsal Head in a Normal Population and Hallux Valgus Patients," Orthopaedics and Traumatology: Surgery and Research, vol. 98, 2012, pp. 677-683.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Rx-Fix Mini Rail External Fixator, Wright Medical Technology, Brochure, Aug. 15, 2014, 2 pages.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Scranton Jr. et al., "Anatomic Variations in the First Ray: Part I. Anatomic Aspects Related to Bunion Surgery," Clinical Orthopaedics and Related Research, vol. 151, Sep. 1980, pp. 244-255.
Siddiqui et al. "Fixation Of Metatarsal Fracture With Bone Plate In A Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
Stableloc External Fixation System, Acumed, Product Overview, Effective date Sep. 2015, 4 pages.
Stahl et al., "Derotation Of Post-Traumatic Femoral Deformities By Closed Intramedullary Sawing," Injury, vol. 37, No. 2, Feb. 2006, pp. 145-151, (Abstract Only).
Talbot et al.," Assessing Sesamoid Subluxation: How Good is the AP Radiograph?," Foot and Ankle International, vol. 19, No. 8, Aug. 1998, pp. 547-554.
TempFix Spanning the Ankle Joint Half Pin and Transfixing Pin Techniques, Biomet Orthopedics, Surgical Technique, 2012, 16 pages.
Weber et al., "A Simple System For Navigation Of Bone Alignment Osteotomies Of The Tibia," International Congress Series, vol. 1268, Jan. 2004, pp. 608-613, (Abstract Only).
Whipple et al., "Zimmer Herbert Whipple Bone Screw System: Surgical Techniques for Fixation of Scaphoid and Other Small Bone Fractures," Zimmer, 2003, 59 pages.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Yasuda et al., "Proximal Supination Osteotomy of the First Metatarsal for Hallux Valgus," Foot and Ankle International, vol. 36, No. 6, Jun. 2015, pp. 696-704.
Chang et al., "Lapidus Arthrodesis: A Different Perspective," Journal of the American Podiatric Medical Association, vol. 84, No. 6, Jun. 1994, pp. 281-288.
Horton et al., "Deformity Correction and Arthrodesis of the Midfoot with a Medial Plate," Foot & Ankle, vol. 14, No. 9, Nov./Dec. 1993, pp. 493-499.

\* cited by examiner

INTRA-OSSEOUS PLATE SYSTEM AND METHOD

RELATED APPLICATION

This application is a continuation of U.S. patent application Ser. No. 16/877,159, filed May 18, 2020, which is a continuation of U.S. patent application Ser. No. 15/148,774, filed May 6, 2016 and issued as U.S. Pat. No. 10,653,467, on May 19, 2020, which claims the benefit of U.S. Provisional Application Ser. No. 62/157,561, filed May 6, 2015. The entire contents of each of these applications are incorporated herein by reference.

TECHNICAL FIELD

This disclosure relates generally to bone plate devices and methods for fixing bone using plate devices.

BACKGROUND

Bones, such as the bones of a foot, may be anatomically misaligned. In certain circumstances, surgical intervention is required to correctly align the bones to reduce patient discomfort and improve patient quality of life. Surgical intervention may involve cutting one or more of the misaligned bones and then physically realigning the bones into an anatomically corrected position. A bone plate or multiple bone plates may be used to hold the bones in the anatomically corrected position, helping to prevent the bones from shifting back to their misaligned position.

SUMMARY

In general, this disclosure is directed to bone fixation systems and techniques for fixating bones. In some examples, a bone plating system includes an intra-osseous support structure configured to be placed in an opening formed between adjacent bones. For example, during a tarsal-metatarsal fusion procedure in which a first metatarsal is realigned with respect to a second metatarsal, the intra-osseous support structure may be placed within the osseous tissue of the first metatarsal and the medial cuneiform, spanning the tarsal-metatarsal joint. An opening or groove may be formed in the end of the first metatarsal facing the medial cuneiform and also in the end of the medial cuneiform facing the first metatarsal, providing cavities in which opposed ends of the intra-osseous support structure are inserted. One or more fasteners can be used to secure the intra-osseous support structure to the bones in which the fastener is inserted. For instance, in the example of a tarsal-metatarsal fusion procedure, a fastener may be inserted into the medial cuneiform (e.g., from the dorsal toward the plantar side), securing the intra-osseous support structure to the medial cuneiform. A second fastener can be inserted into the first metatarsal (e.g., from the dorsal toward the plantar side), securing the intra-osseous support structure to the first metatarsal.

In some applications, a bone plate is also applied on exterior surfaces of the bone portions into which the intra-osseous support structure is inserted. For example, one or more flat or curved bone plates may be applied to exterior surfaces of bone portions containing the intra-osseous support structure. Depending on the configuration, the exterior bone plate(s) may be in compression while the intra-osseous support structure is in tensions under load, providing a balanced fixation system to effectively fixation opposed portions of bone.

In one example, a bone plating system is described that includes a fastener having a length and an intra-osseous support structure. The example specifies that the intra-osseous support structure is configured to be placed in an opening formed in a first bone portion and a second bone portion and has an aperture to receive the fastener.

In another example, a method of plating a bone is described. The method includes forming an opening in a first bone portion and a second bone portion and placing an intra-osseous support structure in the opening. The method further includes inserting a first fastener through the first bone portion and into the intra-osseous support structure and inserting a second fastener through the second bone portion and into the intra-osseous support structure.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Embodiments of the invention include a bone plating system. Embodiments of the system can be useful for providing structural support to bones subject to a surgical procedure, such as a bone alignment, osteotomy, fracture repair, and/or fusion procedure. Such a procedure may be performed, for example, on bones (e.g., adjacent bones separated by a joint or different portions of a single bone separated by a fracture) in the foot or hand. In one example, the procedure can be performed to correct an alignment between a metatarsal (e.g., a first metatarsal) and a cuneiform (e.g., a first cuneiform), such as a bunion correction. An example of such a procedure is a lapidus procedure. In another example, the procedure can be performed by modifying an alignment of a metatarsal (e.g., a first metatarsal). An example of such a procedure is a basilar metatarsal osteotomy procedure.

Figure 1:
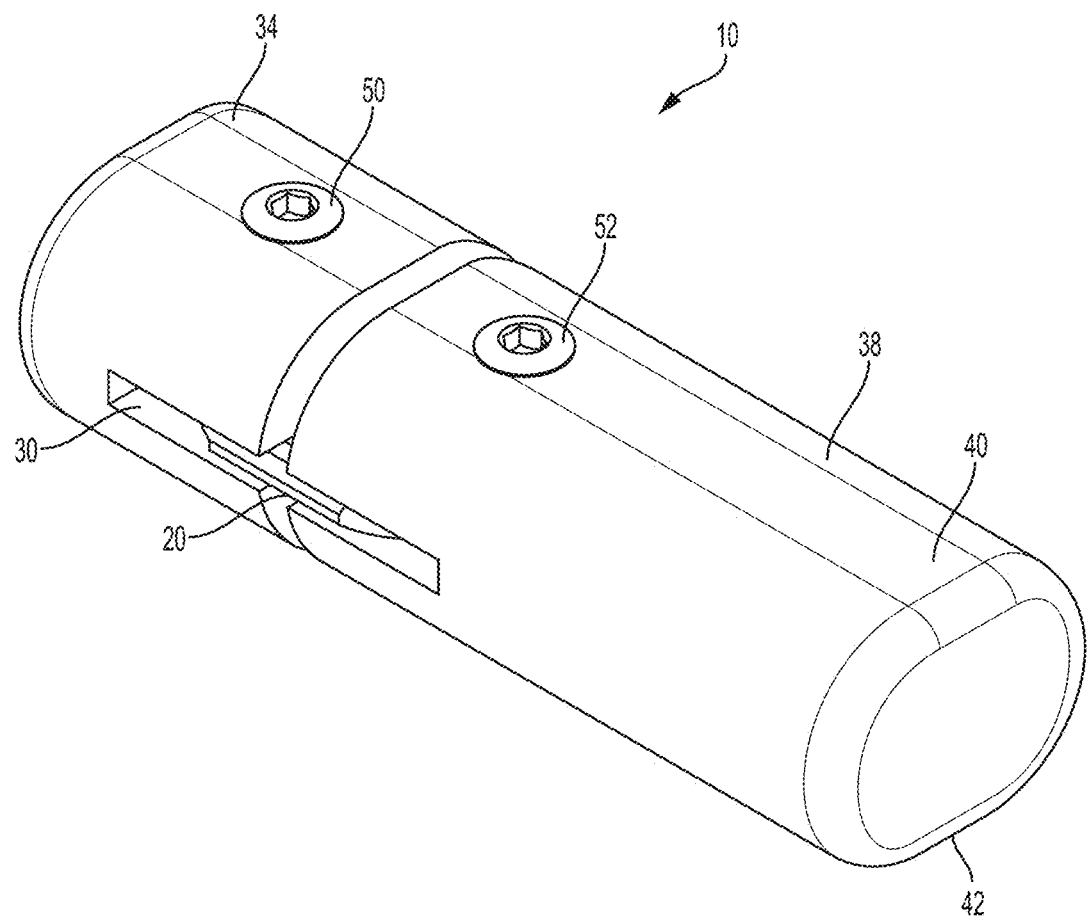
FIG. 1 is a perspective view of a bone plating system in accordance with an embodiment of the invention.

As shown in FIG. 1, embodiments of the bone plating system 10 include an intra-osseous support structure 20. As shown, the intra-osseous support structure can be adapted to be positioned intra-osseously. In such embodiments, the intra-osseous support structure is positioned within a thickness of a bone, such that both of its major surfaces face bone (e.g., cancellous bone). In the embodiment shown, the intra-osseous support structure 20 is adapted to be positioned within an opening 30 of a first bone portion 34 and a second bone portion 38, the opening leading to a cavity or void within the respective bone portions. As shown, in a bone portion having a dorsal surface 40 and a plantar surface 42, the opening can be formed closer to the plantar surface than the dorsal surface (e.g., between about one-half and two-thirds through the thickness of the bone). In certain embodiments, the opening crosses a centerline of one or both bone portions. In such embodiments, the bone defining the opening, and the intra-osseous support structure placed therein, will be in tension under load in situ. Such an intra-osseous support structure can be useful for providing structural support to bones subject to a surgical procedure.

The intra-osseous support structure 20 can include any useful form. In some embodiments, the intra-osseous support structure has a first major surface, a second major surface, and a perimeter edge extending between the first major surface and the second major surface. In the embodiment shown in FIG. 1, the intra-osseous support structure is generally planar as are its first and second major surfaces. The major surfaces can be devoid of any protrusions. In certain embodiments, one or both of the major surfaces can include a surface treatment such as a texture. In some embodiments (not shown), the intra-osseous support structure can include a portion generally perpendicular to a first major surface. For example, the intra-osseous support structure can include a portion that extends from a side (e.g., a medial side) and bends or curves in an upward (e.g., dorsal) or a downward (e.g. plantar) direction around and/or in apposition to a cortical surface of a bone.

In the embodiment shown in FIG. 1, the intra-osseous support structure 20 is connected to a bone portion by at least one fastener 50. In some embodiments, the intra-osseous support structure has a first portion for placement in the first bone portion 34 and a second portion for placement in the second bone portion 38, and at least one aperture (not shown in FIG. 1) to receive a respective fastener can be provided on each portion. In situ, the fastener can extend through a bone surface (e.g., a dorsal surface) and a portion of the thickness of a bone to the intra-osseously positioned support structure and be received into an aperture thereof.

Figure 2:
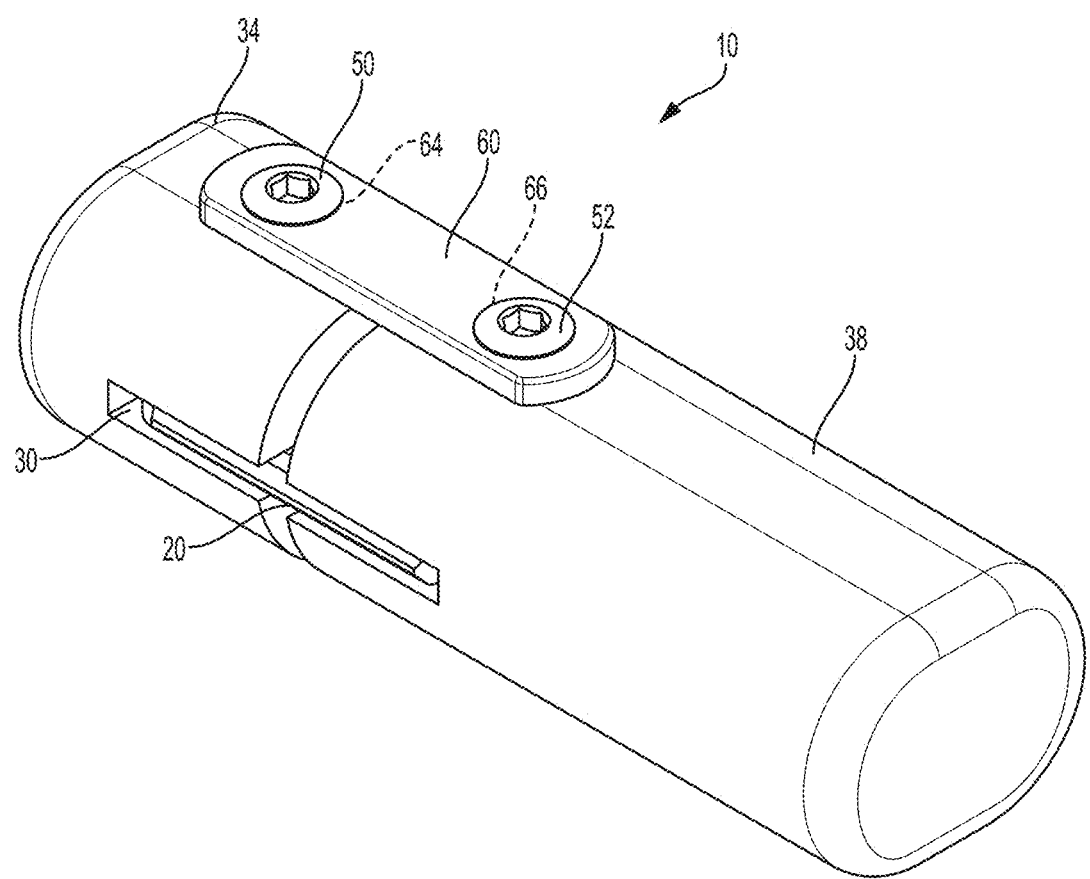
FIG. 2 is a perspective view of a bone plating system in accordance with an embodiment of the invention.
Figure 3:
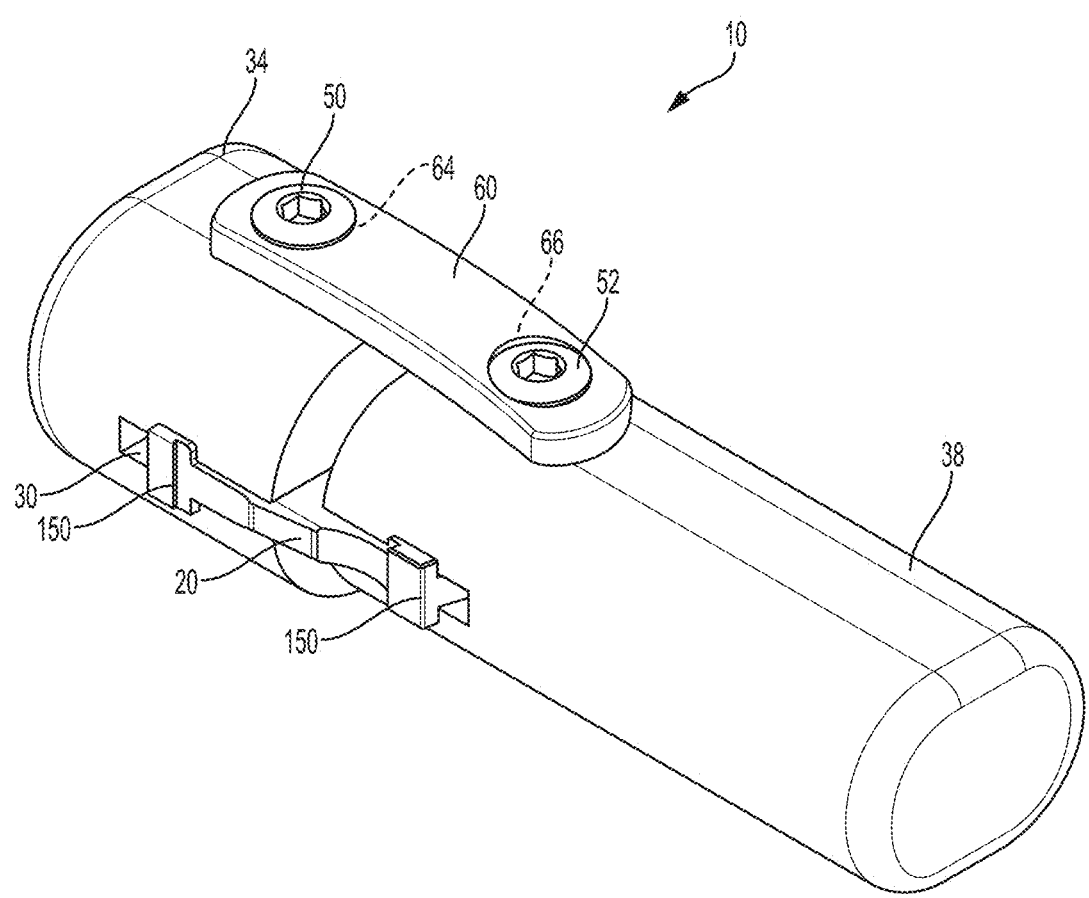
FIG. 3 is a perspective view of a bone plating system in accordance with an embodiment of the invention.

As shown in FIGS. 2 and 3, some embodiments of the bone plating system 10 can include a bone plate 60. In the embodiment shown, the plate is adapted to be positioned on an outer surface of the first bone portion 34 and an outer surface of the second bone portion 38. As shown, in a bone portion having a dorsal surface and a plantar surface, the dorsal surface, and the plate placed thereon, will be in compression under load in situ. Accordingly, some embodiments of the plating system include a plate in compression and an intra-osseous support structure in tension under load in situ. Such a plating system can be useful for providing structural support to bones subject to a surgical procedure.

The bone plate 60 can include any suitable form. In some embodiments, the bone plate has a bone facing surface and a surface opposite the bone facing surface. In certain embodiments, such as the embodiment shown in FIG. 2, the bone plate 60 includes a generally planar member having generally planar surfaces. In other embodiments, such as the embodiment shown in FIG. 3, the bone plate 60 includes a curved shape (about and/or along its longitudinal axis). For example, the surface facing the bone can be concave and the opposite surface can be convex. In certain embodiments, the surface of the bone plate facing the bone may also have at least one protrusion to engage with the surface of the bone.

In embodiments of the plating system having a plate 60, the plate and intra-osseous support structure 20 can be connected to the bone and each other by the at least one fastener 50. In such embodiments, the bone plate 60 can have at least one aperture 64, 66 to receive respective fasteners 50, 52. In the embodiment shown, the bone plate has a first portion for placement on the first bone portion 34 and a second portion for placement on the second bone portion 38. At least one aperture 64, 66 for receiving a respective fastener 50, 52 can be provided on each portion. Further, the intra-osseous support structure 20 can have at least one aperture (not shown in FIGS. 2 and 3) aligned to receive the respective fastener. In situ, the fastener can extend through the bone plate, a surface of the bone, and a portion of the thickness of a bone to the intra-osseously positioned support structure and be received into the aperture thereof. After final placement, in some embodiments, the bone plate and intra-osseous support structure will be generally parallel to each other.

In some embodiments, the aperture in the intra-osseous support structure can include an attachment mechanism configured to engage a fastener. The fastener and attachment mechanism can include any structure suitable for engagement. In some embodiments, the fastener includes a screw, and the attachment mechanism includes a threaded aperture to receive and engage the screw. The attachment mechanism can include guides to facilitate alignment with the fasteners. In some embodiments, the fastener has a length that is less than the thickness of the bone. In certain embodiments, the fastener will have a length between about one-half of the thickness of the bone and the entire thickness of the bone. For example, the fastener can have a length of about two-thirds the thickness of the bone. In some embodiments, the fastener can extend through the aperture of the intra-osseous support structure (optionally engaging an attachment member thereof) and engage bone on one or both sides of the intra-osseous support structure.

Figure 4:
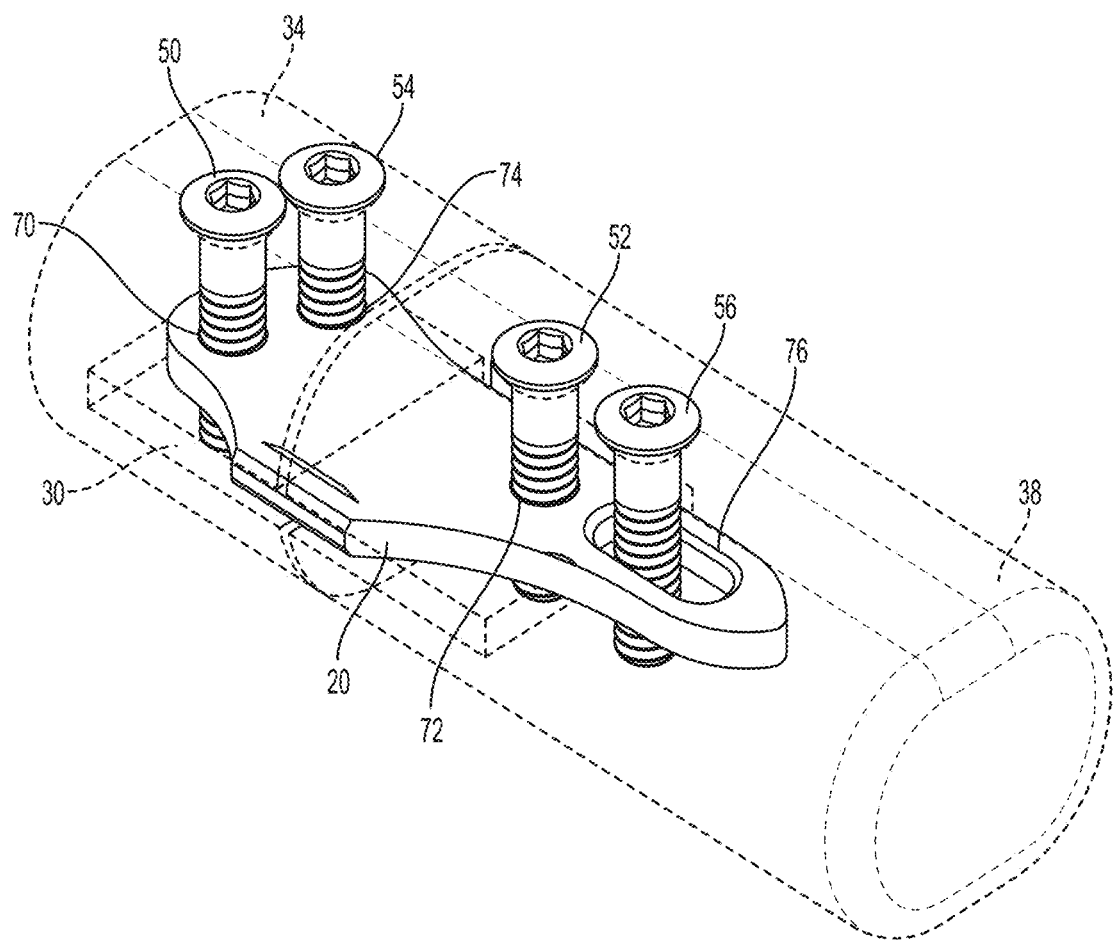
FIG. 4 is a perspective view of a bone plating system in accordance with an embodiment of the invention, with bone portions depicted as transparent.
Figure 5:
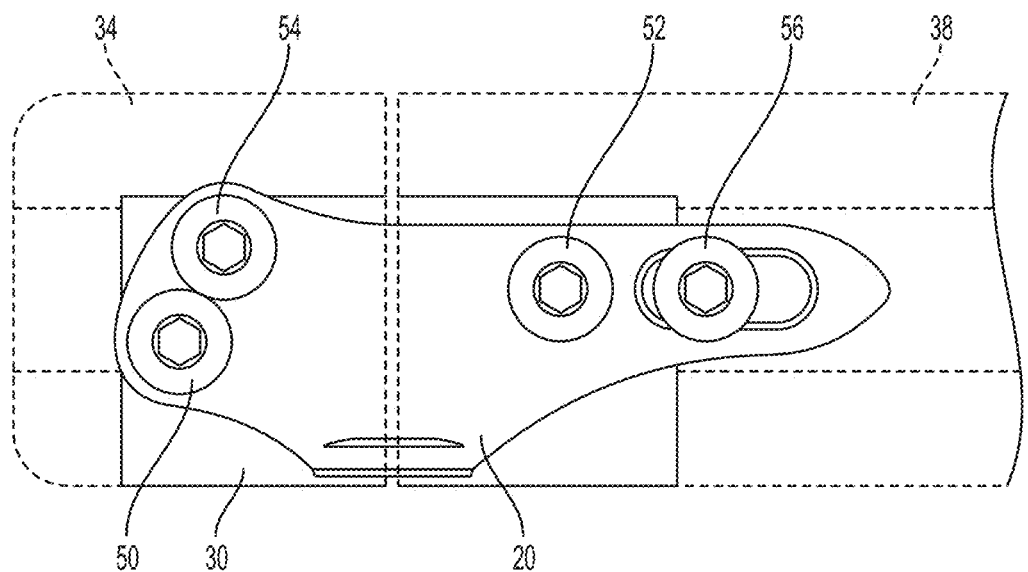
FIG. 5 is a top view of a bone plating system in accordance with an embodiment of the invention, with bone portions depicted as transparent.

Any number of fasteners and respective intra-osseous support structure apertures can be provided. In the embodiment shown in FIGS. 1-3, the intra-osseous support structure 20 includes two apertures to receive two respective fasteners 50, 52. In the embodiment shown in FIGS. 4 and 5, the intra-osseous support structure 20 includes four apertures 70, 72, 74, 76 to receive four respective fasteners 50, 52, 54, 56. In other embodiments, the intra-osseous support structure includes three apertures to receive three respective fasteners. In an embodiment of an intra-osseous support structure having a portion generally perpendicular to a first major surface, such a portion may include one or more apertures for receiving a fastener.

Figure 6:
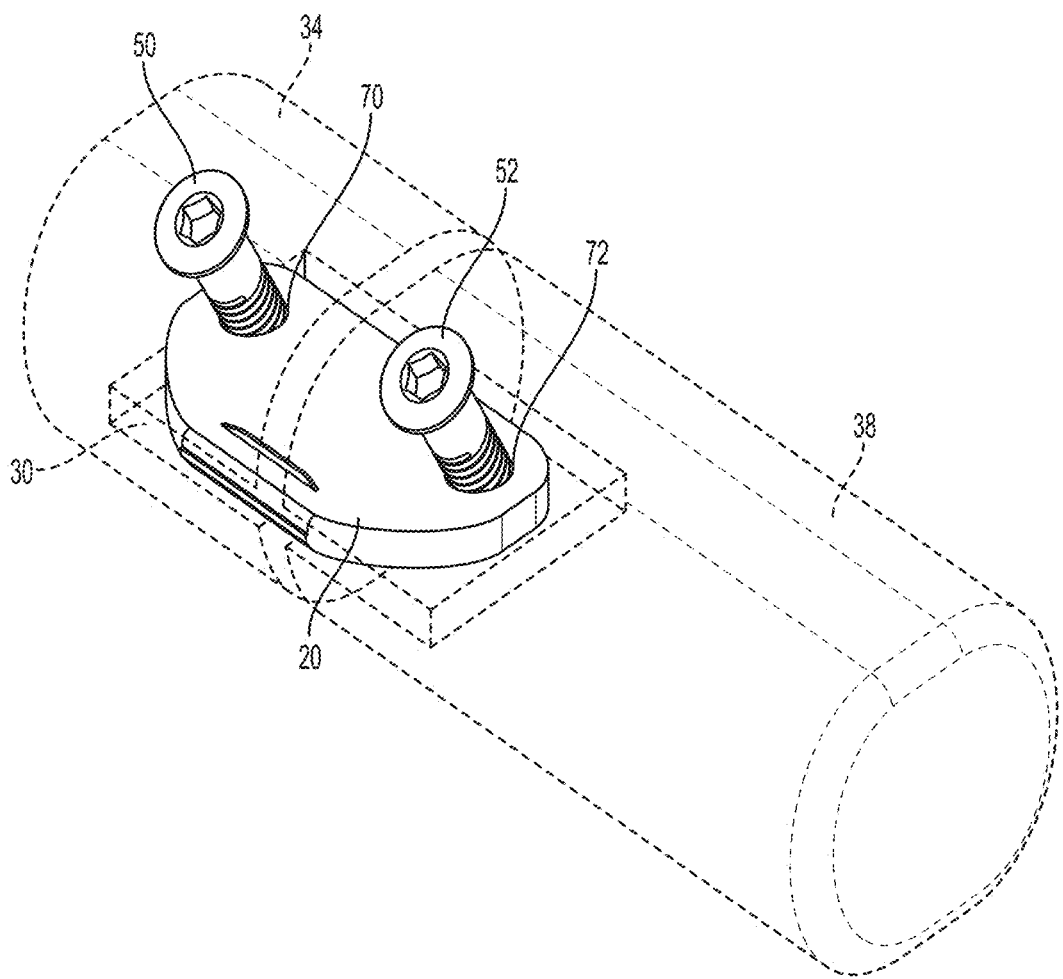
FIG. 6 is a perspective view of a bone plating system in accordance with an embodiment of the invention, with bone portions depicted as transparent.
Figure 7:
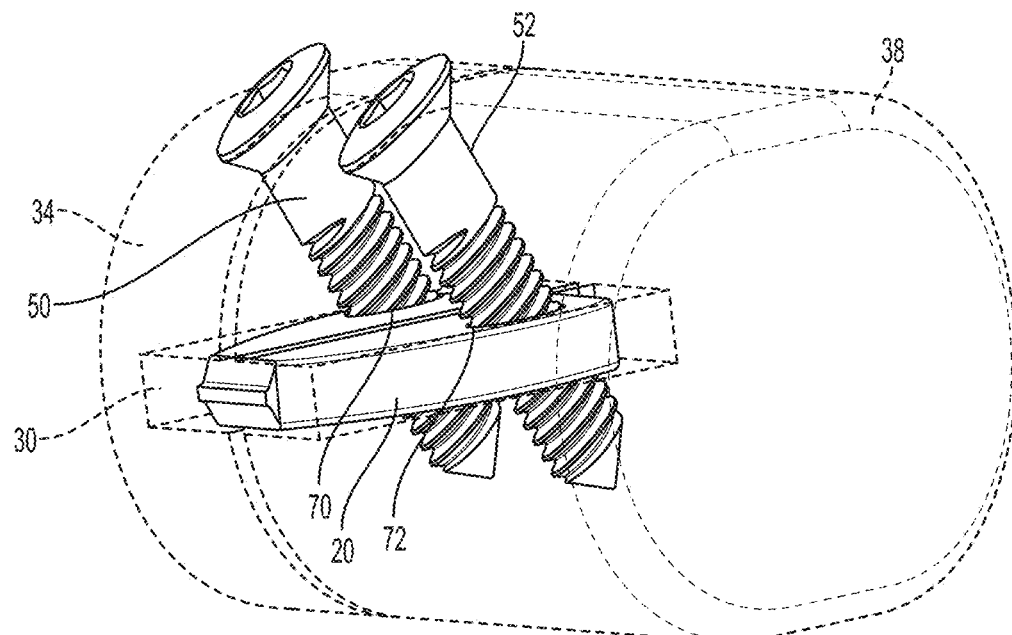
FIG. 7 is a perspective view of a bone plating system in accordance with an embodiment of the invention, with bone portions depicted as transparent.
Figure 8:
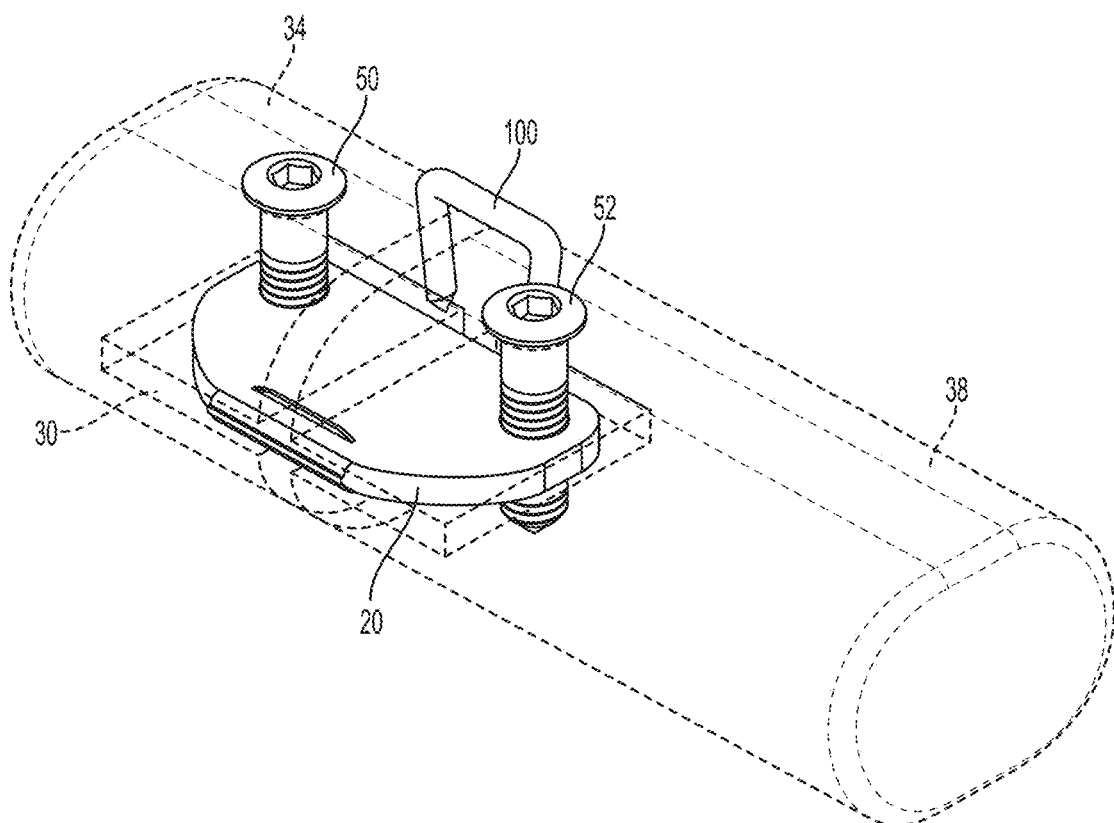
FIG. 8 is a perspective view of a bone plating system in accordance with an embodiment of the invention, with bone portions depicted as transparent.
Figure 9:
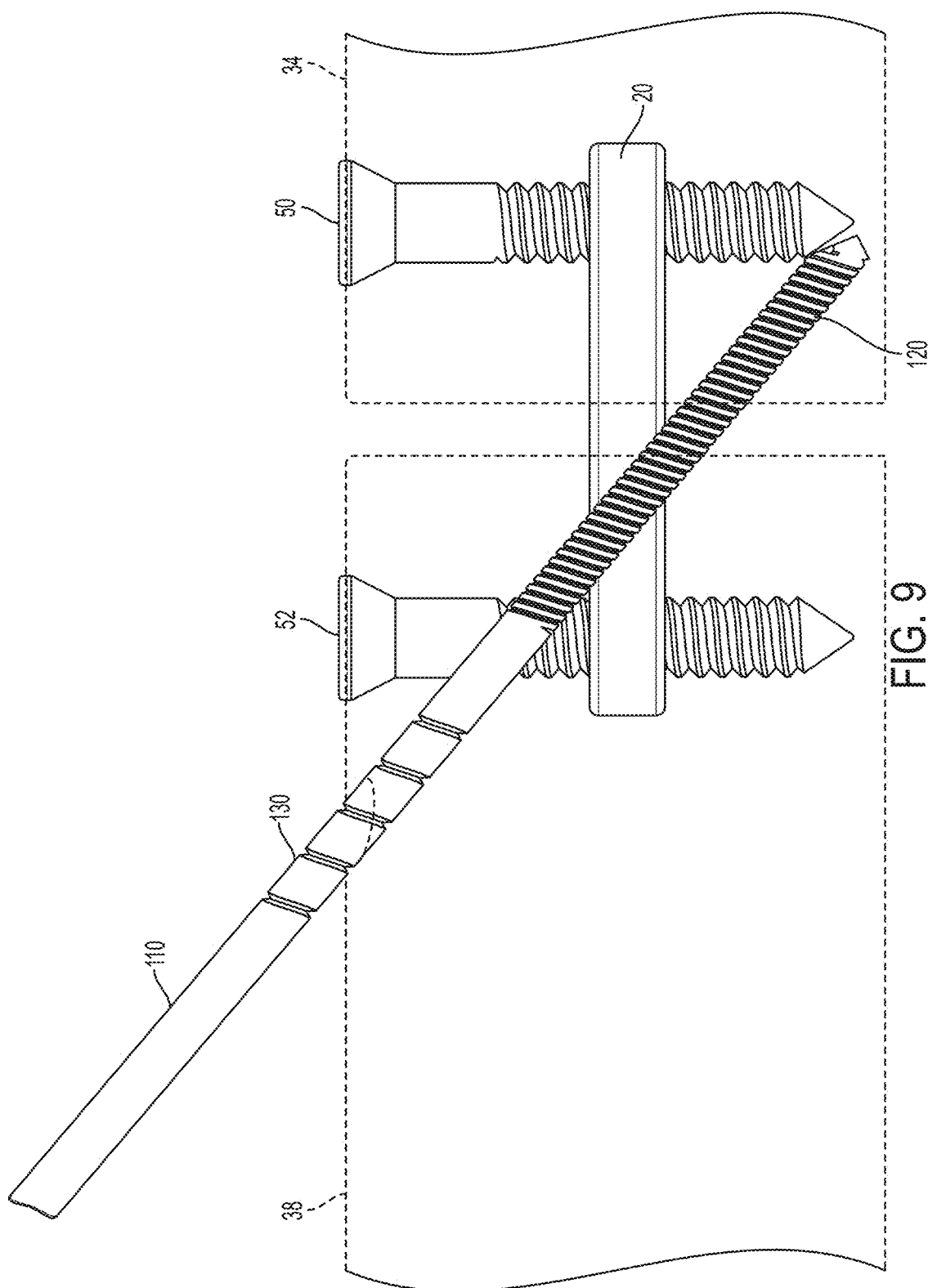
FIG. 9 is a side view of a bone plating system in accordance with an embodiment of the invention, with bone portions depicted as transparent.
Figure 10:
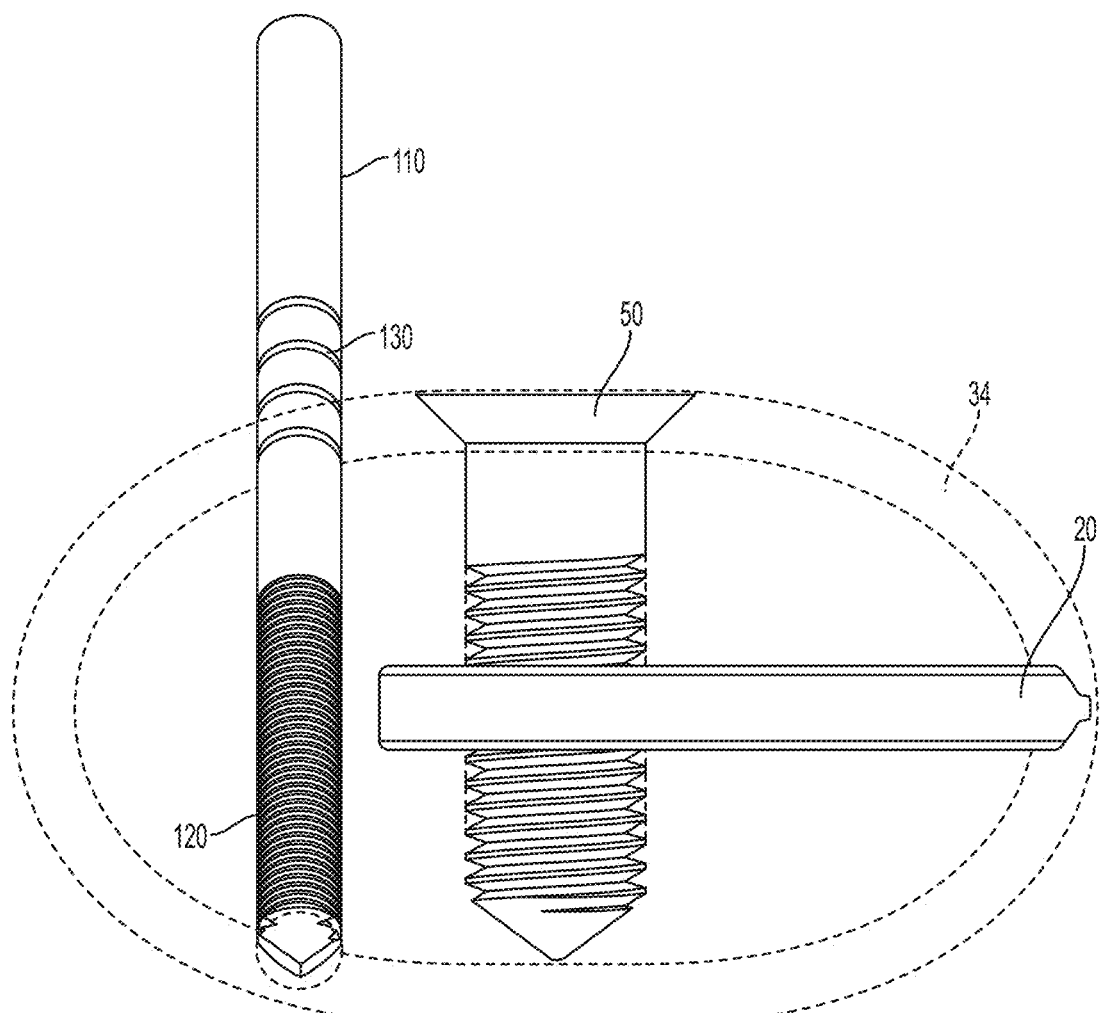
FIG. 10 is an end view of a bone plating system in accordance with an embodiment of the invention, with bone portions depicted as transparent.
Figure 11:
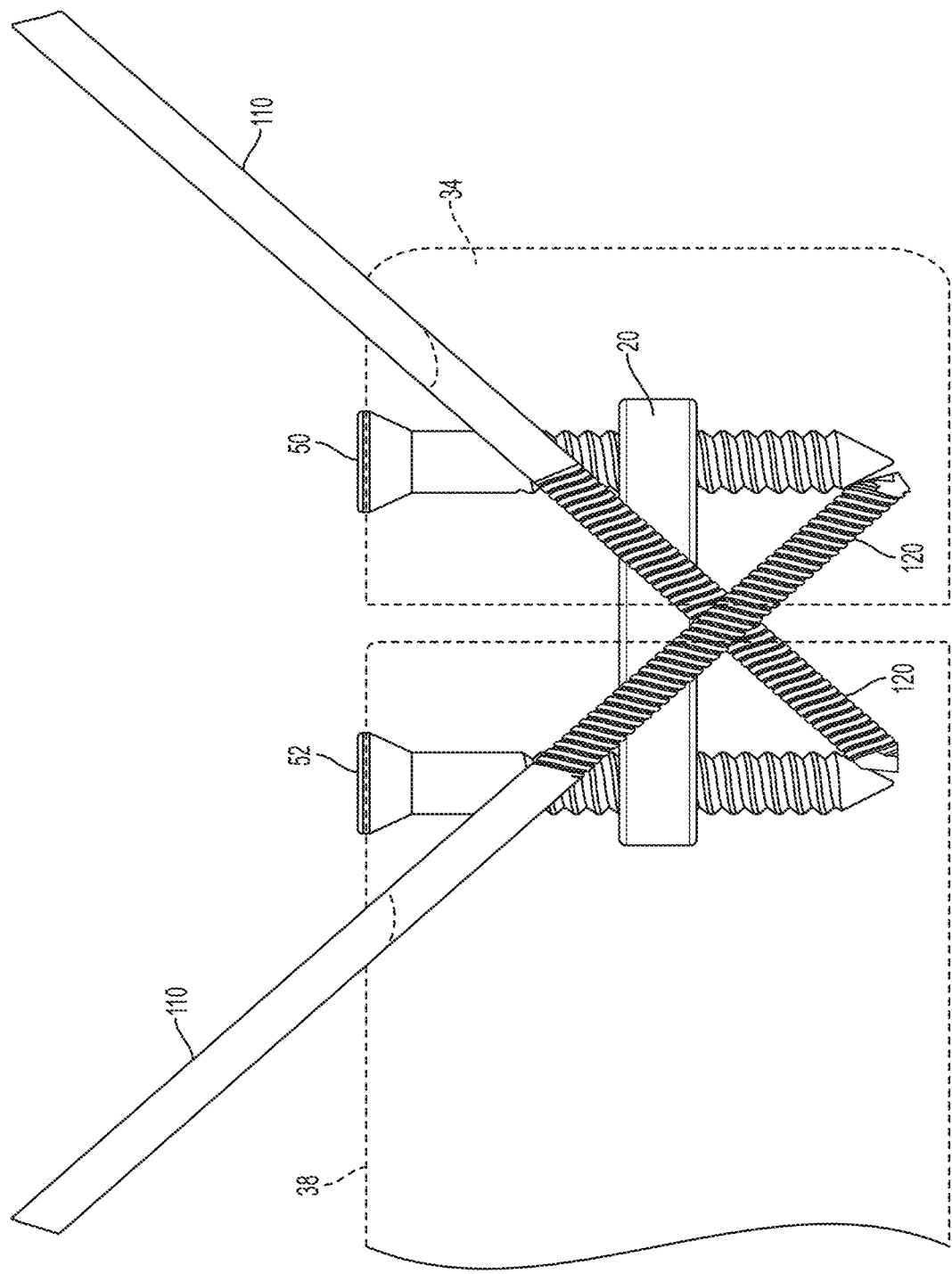
FIG. 11 is a side view of a bone plating system in accordance with an embodiment of the invention, with bone portions depicted as transparent.
Figure 12:
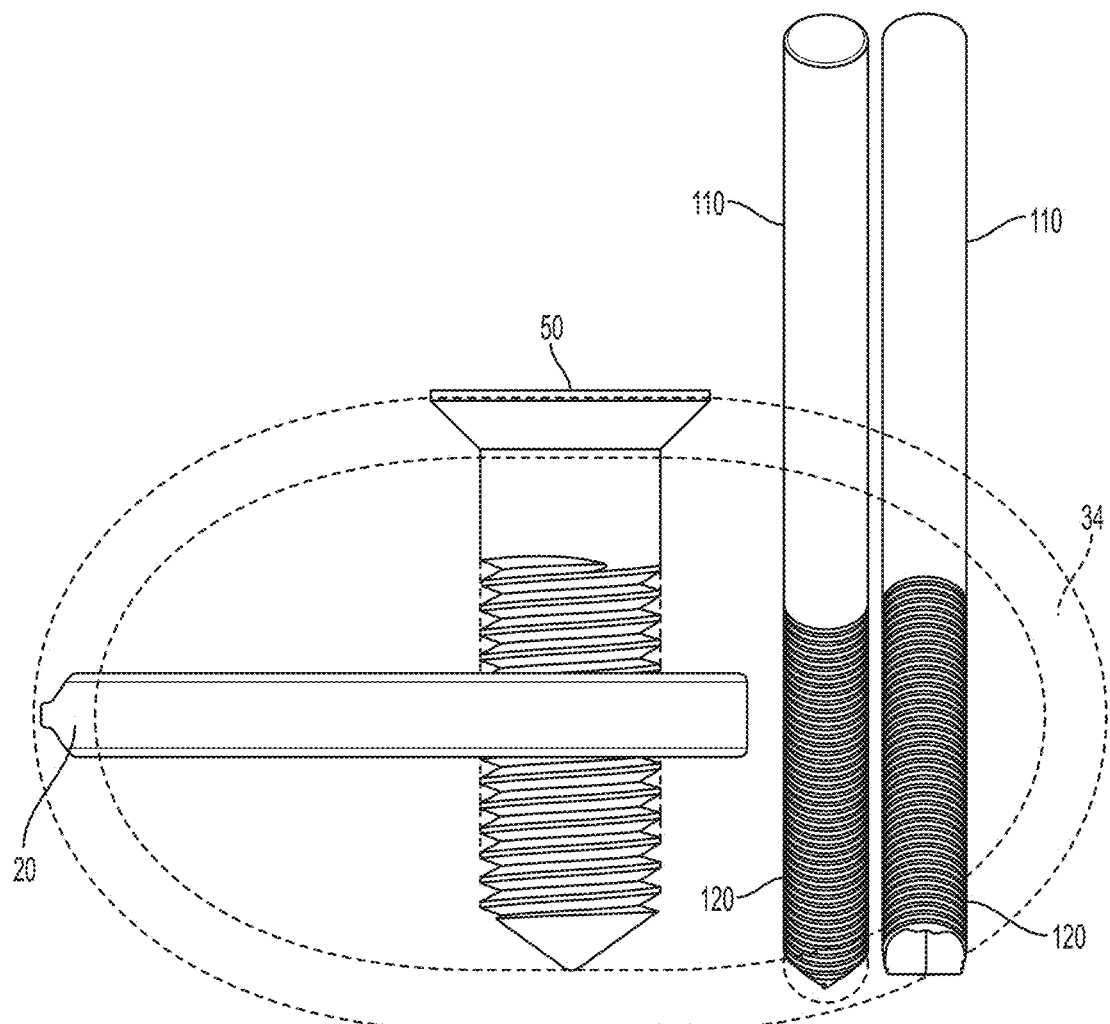
FIG. 12 is an end view of a bone plating system in accordance with an embodiment of the invention, with bone portions depicted as transparent.

The fasteners and respective apertures can be provided in any orientation. In some embodiments, such as the embodiments shown in FIGS. 4, the apertures 70, 72, 74, 76 have a longitudinal axis perpendicular to a first major surface of the intra-osseous support structure 20. In other embodiments, such as the embodiment shown in FIGS. 6 and 7, the apertures 70, 72 have a longitudinal axis that intersects a first major surface of the intra-osseous support structure 20 at a skewed angle (e.g., an angle ranging from about 20 degrees to about 40 degrees from perpendicular). Further, in some embodiments, fasteners 50, 52 can extend from the bone surface and through the bone generally parallel to each other. In other embodiments, first and second fasteners can extend from the bone surface and through the bone at a skewed angle relative to each other. In embodiments of the plating system that include a plate, apertures 64, 66 can be configured such that first and second fasteners 50, 52 can extend from the bone plate 60 generally parallel to each other or at a skewed angle relative to each other.

As shown in FIGS. 8-12, some embodiments of the plating system can include an additional support that does not engage the intra-osseous support structure. Such an additional support can be useful for providing rotational stability to the plated bone portions. In the embodiment shown in FIG. 8, the additional support includes a staple 100 having an end in each bone portion 34, 38. In the example shown in FIGS. 9-10, the additional support includes a pin 110 extending across the bone portions 34, 38 at an angle (e.g., about 45 degrees). In the embodiment shown, the pin 110 includes threads 120 on its distal portion to engage bone. It also includes notches 130 on its proximal portion. The pin can be broken at a desired notch after installation. In the embodiment shown in FIGS. 11 and 12, two pins 110 are provided. As shown, the pins are inserted such that they extend across the bone portions 34, 38 in a crossing pattern, each at an angle (e.g., about 45 degrees).

Figure 13:
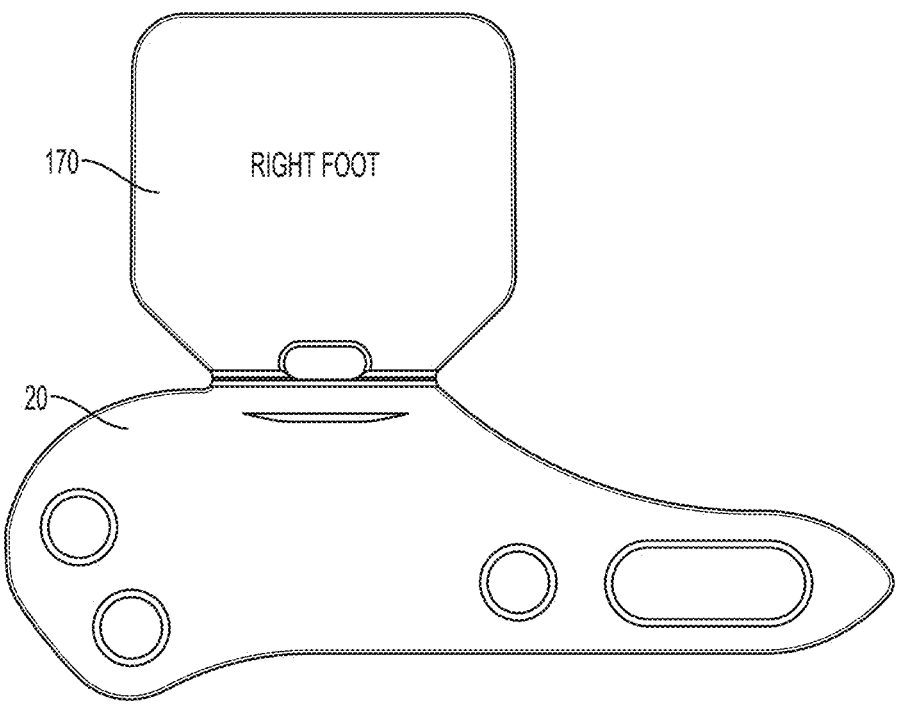
FIG. 13 is a top plan view of an intra-osseous support structure in accordance with an embodiment of the invention.
Figure 14:
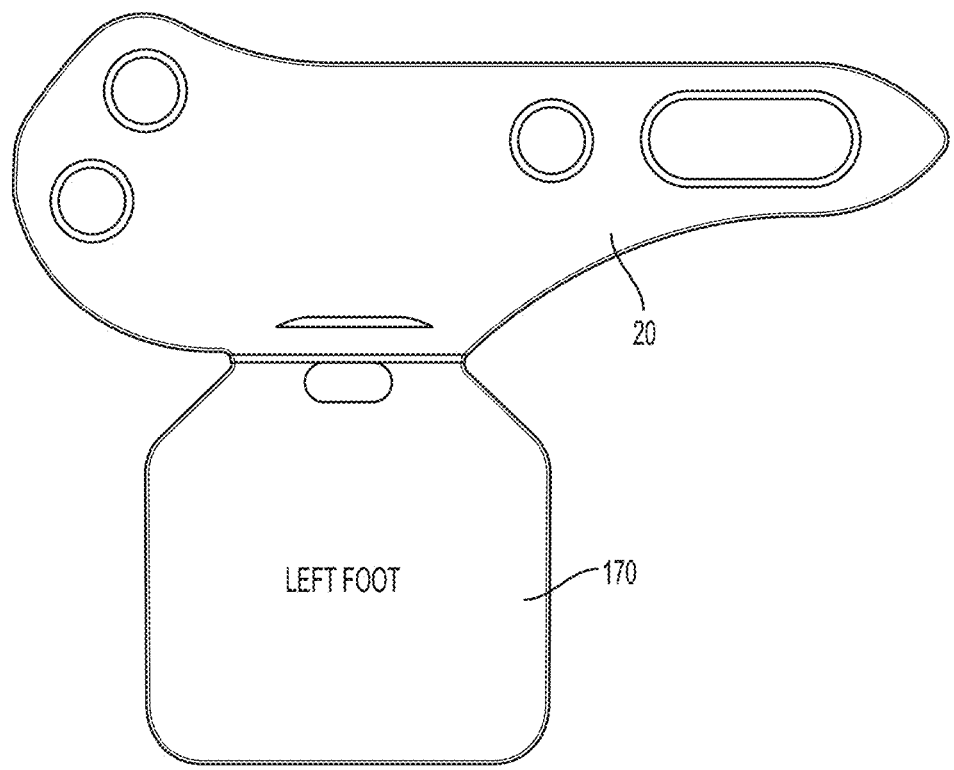
FIG. 14 is a top plan view of an intra-osseous support structure in accordance with an embodiment of the invention.
Figure 15:
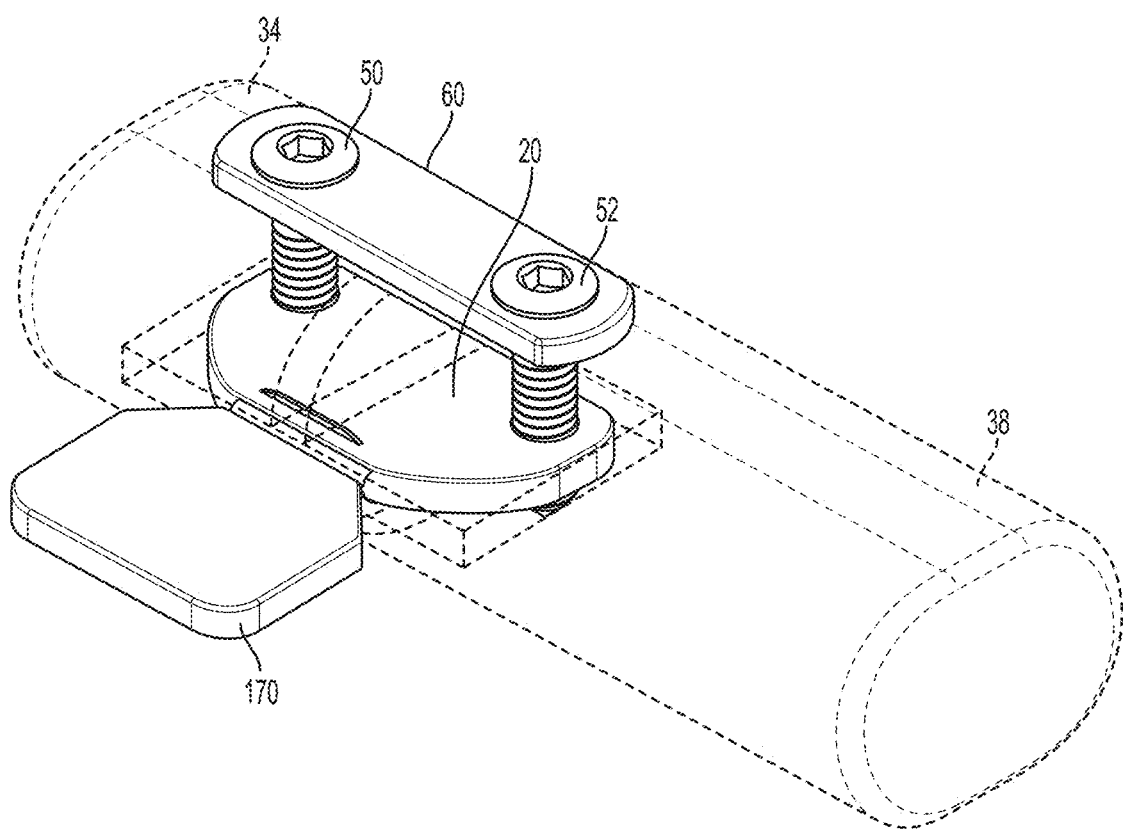
FIG. 15 is a perspective view of a bone plating system in accordance with an embodiment of the invention, with bone portions depicted as transparent.
Figure 16:
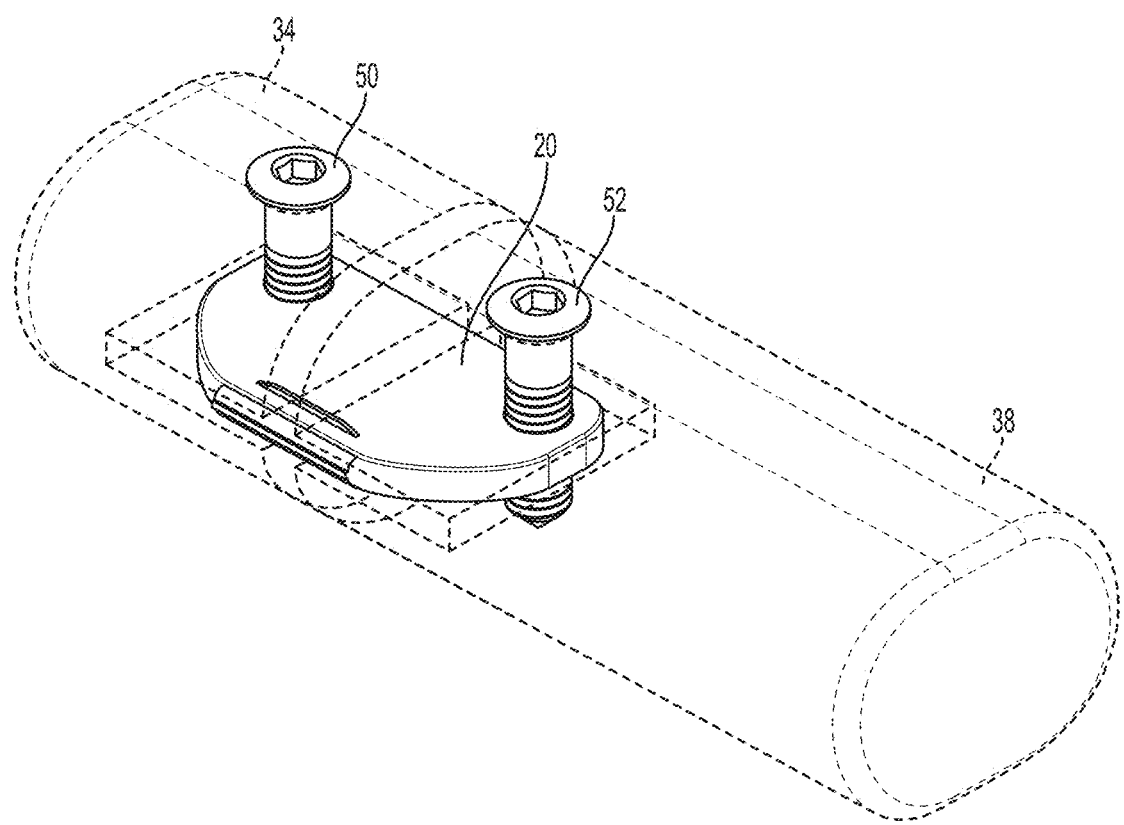
FIG. 16 is a perspective view of a bone plating system in accordance with an embodiment of the invention, with bone portions depicted as transparent.

The plating system can also include features useful for placing the intra-osseous support structure. As shown in FIG. 3, the intra-osseous support structure 20 can include a stop 150 on the perimeter edge that extends past the first major surface or the second major surface. In some embodiments, the stop is on a medial side of the intra-osseous support structure. In other embodiments, as shown in FIG. 13-15, a tab 170 extending beyond the perimeter edge (e.g., on a medial side) can be provided. The tab can be useful for placing the intra-osseous support structure within the bone, and, in some embodiments, can be provided with break seam such that it can be easily removed from the intra-osseous support structure after placement. FIG. 16 shows in intra-osseous support structure 20 with the tab removed.

The plating system can be used to join any bone portions. In one example, the first bone portion and the second bone portion are portions of a single bone separated by a fracture. As a further example, the first bone portion and the second bone portion are portions of a single bone separated by an osteotomy. As another example, the first bone portion and the second bone portion can be portions of two different bones separated by a joint, such as a cuneiform (e.g., medial cuneiform) and a metatarsal (e.g., first metatarsal). In the two-bone example, the intra-osseous support structure can be placed intra-osseously in the cuneiform and the metatarsal in an opening that spans the joint therebetween (e.g., tarsal-metatarsal joint). In such an embodiment, fasteners having a length less than the thickness of the cuneiform and metatarsal, respectively, can be used to connect the intra-osseous support structure to the bones. In embodiments of the plating system having a bone plate, the bone facing surface of the bone plate can be placed facing a dorsal surface of the cuneiform and a dorsal surface of the metatarsal, spanning a joint therebetween, and the fasteners can extend through apertures defined by the plate.

Embodiments of the invention also include methods of plating a bone, such as with the embodiments of bone plating systems described herein. Note the order of steps as described is only exemplary unless otherwise indicated. In some embodiments, after preparing the surgical area, the method can include the step of forming an opening in a first bone portion and a second bone portion. The opening can be formed from a side of the bone. The opening can be formed generally parallel with a longitudinal axis of the bone, or may be formed at an angle with respect to such longitudinal axis such that it crosses the longitudinal axis. The opening can be formed, e.g., by a saw, drill, mill, box chisel, router, or the like.

The method can also include the steps of placing an intra-osseous support structure in the opening and aligning it in a desired position. In some embodiments, the intra-osseous support structure can be placed generally parallel to a longitudinal axis of the bone (e.g., toward a tension side of the longitudinal axis. In other embodiments, the intra-osseous support structure can be placed at a skewed angle relative to the longitudinal axis of the bone, such that it crosses the longitudinal axis of the bone. In such embodiments, at least a portion of the intra-osseous support structure will reside on a tension side of the longitudinal axis and another portion will reside on a compression side of the longitudinal axis. The method can also include the steps of inserting a first fastener through a first bone portion and engaging the first fastener with the intra-osseous support structure, and inserting a second fastener through a second bone portion and engaging the second fastener with the intra-osseous support structure to secure the plating system to the bone. In some embodiments, the step of placing the intra-osseous support structure in the opening includes placing a stop in apposition to the first bone portion or the second bone portion. In embodiments of intra-osseous support structures having tabs, the method can also include removing the tab after placement of the support structure. Embodiments of the method can also include attaching an additional support structure to the first bone portion and the second bone portion.

In some embodiments, the method can also include the step of forming a first hole in the first bone portion from the first surface and toward an opposite surface and forming a second hole in the second bone portion from the second surface and toward an opposite surface. The first and second holes and the opening can intersect. The first and second holes can be formed, for example, with hand-driven or powered drills. In such embodiments, the fasteners can be inserted through the holes to engage an intra-osseous support structure placed within the opening.

Embodiments of the method also include placing a bone plate having a first portion in apposition to a first surface of a first bone portion and a second portion in apposition to a second surface of a second bone portion, the bone plate having a first aperture in the first portion and a second aperture in the second portion. The bone plate can be initially held in position by pins and/or protrusions. The fasteners can be inserted through apertures defined by the plate.

Thus, embodiments of the invention are disclosed. Although the present invention has been described with reference to certain disclosed embodiments, the disclosed embodiments are presented for purposes of illustration and not limitation, and other embodiments of the invention are possible. One skilled in the art will appreciate that various changes, adaptations, and modifications may be made without departing from the spirit of the invention.

The invention claimed is:

1. A method comprising:
performing an osteotomy on a metatarsal to separate the metatarsal into a first metatarsal portion and a second metatarsal portion;
adjusting an alignment of the first metatarsal portion relative to the second metatarsal portion;
placing a first portion of an intra-osseous support structure in the first metatarsal portion, wherein the intra-osseous support structure comprise a plate having a first major surface, a second major surface, and perimeter edge extending between the first major surface and the second major surface, and placing the first portion of the intra-osseous support structure in the first metatarsal portion comprises positioning the first portion of the intra-osseous support structure within an intra-osseous region of the first metatarsal portion with the first major surface and the second major surface each facing cancellous bone of the first metatarsal portion; and
connecting a second portion of the intra-osseous support structure to the second metatarsal portion using at least one fastener.

2. The method of claim 1, wherein connecting the second portion of the intra-osseous support structure to the second metatarsal portion comprises inserting a screw through an outer surface of the second metatarsal portion.

3. The method of claim 2, further comprising forming a hole in the second metatarsal portion from the outer surface toward an opposite surface, wherein inserting the screw through the outer surface of the second metatarsal portion comprises inserting the screw into the hole.

4. The method of claim 2, wherein the second portion of the intra-osseous support structure comprises a threaded aperture, and inserting the screw through the outer surface of the second metatarsal portion comprises inserting the screw into the threaded aperture.

5. The method of claim 1, wherein connecting the second portion of the intra-osseous support structure to the second metatarsal portion using at least one fastener comprises inserting the at least one fastener through a thickness of the second metatarsal portion less than an entire thickness of the second metatarsal portion.

6. The method of claim 5, wherein the thickness of the second metatarsal portion is within a range from one-half to two-thirds of the entire thickness of the second metatarsal portion.

7. The method of claim 1, further comprising inserting a fastener into the first portion of the intra-osseous support structure.

8. The method of claim 7, wherein inserting the fastener into the first portion of the intra-osseous support structure comprises inserting the fastener through an outer surface of the first metatarsal portion.

9. The method of claim 8, wherein inserting the fastener through the outer surface of the first metatarsal portion comprises engaging the fastener with the intra-osseous support structure in the first metatarsal portion.

10. The method of claim 7, wherein inserting the fastener into the first portion of the intra-osseous support structure comprises inserting the fastener through a thickness of the first metatarsal portion less than an entire thickness of the first metatarsal portion.

11. The method of claim 7, wherein the fastener comprises a first fastener, and further comprising inserting a second fastener into the first portion of the intra-osseous support structure.

12. The method of claim 1, further comprising placing the second portion of the intra-osseous support structure in the second metatarsal portion.

13. The method of claim 12, further comprising forming an opening in the second metatarsal portion, wherein placing the second portion of the intra-osseous support structure in the second metatarsal portion comprises placing the second portion of the intra-osseous support structure in the opening in the second metatarsal portion.

14. The method of claim 1, wherein placing the first portion of the intra-osseous support structure in the first metatarsal portion and connecting the second portion of the intra-osseous support structure to the second metatarsal portion comprises fusing the first metatarsal portion to the second metatarsal portion.

15. The method of claim 1, further comprising forming an opening in the intra-osseous region of the first metatarsal portion, wherein placing the first portion of the intra-osseous support structure in the first metatarsal portion comprises placing the first portion of the intra-osseous support structure in the opening in the first metatarsal portion.

16. The method of claim 1, wherein the at least one fastener comprises two fasteners, and connecting the second portion of the intra-osseous support structure to the second metatarsal portion using at least one fastener comprises connecting the second portion of the intra-osseous support structure to the second metatarsal portion using two fasteners.

17. The method of claim 1, wherein the metatarsal is a first metatarsal.

18. The method of claim 1, wherein the intra-osseous support structure is planar.

19. The method of claim 1, wherein the intra-osseous support structure includes one portion that curves and/or extends from a side relative to an other portion.

20. A method comprising:
performing an osteotomy on a metatarsal to separate the metatarsal into a first metatarsal portion and a second metatarsal portion;
adjusting an alignment of the first metatarsal portion relative to the second metatarsal portion; and
fixating the first metatarsal portion relative to the second metatarsal portion for fusion using a structure that includes a first portion and a second portion, the first portion comprising a plate having a first major surface, a second major surface, and perimeter edge extending between the first major surface and the second major surface, the first portion being configured to be positioned intra-osseously, and the second portion including at least one aperture extending through a thickness of the structure configured to receive a screw, wherein fixating the first metatarsal portion relative to the second metatarsal portion comprises inserting the first portion of the structure within an intra-osseous region of the first metatarsal portion with the first major surface and the second major surface each facing cancellous bone of the first metatarsal portion and screwing at least one screw into the at least one aperture of the second portion of the structure and into the second metatarsal portion.

21. The method of claim 20, wherein the at least one aperture comprises a threaded aperture, and screwing at least one screw into the at least one aperture of the second portion of the structure comprises screwing at least one screw into the threaded aperture of the second portion of the structure.

22. The method of claim 20, wherein the at least one aperture comprises two apertures and the at least one screw comprises two screws, and screwing at least one screw into the at least one aperture of the second portion of the structure and into the second metatarsal portion comprises screwing two screws into the two apertures of the second portion of the structure and into the second metatarsal portion.

23. The method of claim 20, wherein the first portion comprises at least one aperture configured to receive a screw, and further comprising screwing at least one screw into the at least one aperture of the first portion of the structure positioned within the first metatarsal portion.

24. The method of claim 23, wherein the first portion comprises two apertures, and screwing at least one screw into the at least one aperture of the first portion of the structure positioned within the first metatarsal portion comprises screwing a screw into each of the two apertures of the first portion of the structure positioned within the first metatarsal portion.

25. The method of claim 20, wherein the metatarsal is a first metatarsal.

* * * * *